(12) United States Patent
Nakhasi et al.

(10) Patent No.: US 8,221,818 B2
(45) Date of Patent: Jul. 17, 2012

(54) COMPOSITION WITH HEALTH AND NUTRITION PROMOTING CHARACTERISTICS, CONTAINING INTERESTIFIED LIPIDS AND PHYTOSTEROL, AND RELATED METHODS

(75) Inventors: Dilip K. Nakhasi, Bourbonnals, IL (US); Roger L. Daniels, Manhattan, IL (US)

(73) Assignee: Bunge Oils, Inc., St. Louis, MO (US)

( * ) Notice: Subject to any disclaimer, the term of this patent is extended or adjusted under 35 U.S.C. 154(b) by 1489 days.

(21) Appl. No.: 10/598,215

(22) PCT Filed: Mar. 2, 2005

(86) PCT No.: PCT/US2005/006745
§ 371 (c)(1),
(2), (4) Date: Aug. 21, 2006

(87) PCT Pub. No.: WO2005/093027
PCT Pub. Date: Oct. 6, 2005

(65) Prior Publication Data
US 2007/0141221 A1     Jun. 21, 2007

Related U.S. Application Data

(63) Continuation-in-part of application No. 10/795,843, filed on Mar. 8, 2004.

(51) Int. Cl.
*A23D 7/00*     (2006.01)
*A23D 9/00*     (2006.01)
(52) U.S. Cl. .................. 426/601; 426/606; 426/607
(58) Field of Classification Search .................. None
See application file for complete search history.

(56) References Cited

U.S. PATENT DOCUMENTS

| | | | |
|---|---|---|---|
| 3,006,771 A | 10/1961 | Babayan | |
| 3,450,819 A | 6/1969 | Babayan et al. | |
| 3,592,661 A | 7/1971 | Seiden | |
| 3,595,673 A | 7/1971 | Seiden | |
| 4,832,975 A | 5/1989 | Yang | |
| 4,952,606 A | 8/1990 | Babayan et al. | |
| 5,288,512 A | 2/1994 | Seiden | |
| 5,434,278 A | 7/1995 | Pelloso et al. | |
| 5,908,654 A | 6/1999 | Cain et al. | |
| 5,908,655 A | 6/1999 | Doucet | |
| 5,998,396 A | 12/1999 | Nakano et al. | |
| 6,031,118 A | 2/2000 | van Amerongen et al. | |
| 6,087,353 A | 7/2000 | Stewart et al. | |
| 6,106,886 A | 8/2000 | van Amerongen et al. | |
| 6,113,972 A | 9/2000 | Corliss et al. | |
| 6,117,475 A | 9/2000 | van Amerongen et al. | |
| 6,124,486 A | 9/2000 | Cherwin et al. | |
| 6,139,897 A | 10/2000 | Goto et al. | |
| 6,149,961 A | 11/2000 | Kepplinger et al. | |
| 6,162,483 A | 12/2000 | Wester | |
| 6,174,560 B1 | 1/2001 | Miettenen et al. | |
| 6,190,720 B1 | 2/2001 | Yuan et al. | |
| 6,228,407 B1 | 5/2001 | Kepplinger et al. | |
| 6,238,926 B1 | 5/2001 | Liu et al. | |
| 6,274,574 B1 | 8/2001 | Akashe et al. | |
| 6,277,431 B1 | 8/2001 | Berry et al. | |
| 6,326,050 B1 | 12/2001 | Goto et al. | |
| 6,376,482 B2 | 4/2002 | Akashe et al. | |
| 6,399,138 B1 | 6/2002 | Cain et al. | |
| 6,410,078 B1 | 6/2002 | Cain et al. | |
| 6,413,571 B1 | 7/2002 | Liu | |
| 6,531,463 B1 | 3/2003 | Yliruusi et al. | |
| 6,562,395 B2 | 5/2003 | Wester et al. | |
| 6,576,285 B1 | 6/2003 | Bader et al. | |
| 6,589,588 B1 | 7/2003 | Wester et al. | |
| 6,623,780 B1 | 9/2003 | Stevens et al. | |
| 6,793,959 B2 | 9/2004 | Nakhasi et al. | |
| 6,800,317 B2 | 10/2004 | Wester et al. | |
| 6,827,963 B2 | 12/2004 | Aoyama | |
| 6,835,408 B2 | 12/2004 | Takeuchi et al. | |
| 6,929,816 B2 | 8/2005 | Wester | |
| 2002/0001660 A1 | 1/2002 | Takeuchi et al. | |
| 2002/0012722 A1 | 1/2002 | Prosise et al. | |
| 2002/0015759 A1 | 2/2002 | Prosise et al. | |
| 2002/0015760 A1 | 2/2002 | Prosise et al. | |
| 2002/0015761 A1 | 2/2002 | Prosise et al. | |
| 2002/0031595 A1 | 3/2002 | Wester et al. | |
| 2002/0034574 A1 | 3/2002 | Prosise et al. | |
| 2002/0045000 A1 | 4/2002 | Nakajima et al. | |

(Continued)

FOREIGN PATENT DOCUMENTS

| | | |
|---|---|---|
| WO | WO 98/19556 | 5/1998 |
| WO | WO 00/03609 | 1/2000 |
| WO | WO 98/06405 A1 | 9/2000 |
| WO | WO 01/13733 A1 | 3/2001 |
| WO | WO 01/32029 A2 | 5/2001 |
| WO | WO 01/32035 A1 | 5/2001 |
| WO | WO 01/91587 A2 | 12/2001 |
| WO | WO 02/16534 | 2/2002 |
| WO | WO 02/055639 A1 | 7/2002 |

OTHER PUBLICATIONS

St-Onge, Ross, Parsons and Jones, "Medium Chain Triglycerides Increase Energy Expenditure and Decrease Adiposity in Overweight Men," Obesity Research, vol. 11 No. 3, Mar. 2003, pp. 395-402.

St-Onge and Jones, "Phytosterols and Human Lipid Metabolism: Efficacy, Safety, and Novel Foods," Lipids, vol. 38, No. 4, Apr. 2003, pp. 367-375, AOCS Press.

(Continued)

*Primary Examiner* — Elizabeth Gwartney
(74) *Attorney, Agent, or Firm* — Cook Alex Ltd.

(57) ABSTRACT

Medium chain triglyceride oils are interesterified with long chain domestic oils in order to form interesterified structured lipids. These structured lipids find special application in combination with phytosterols to provide compositions and methods for enhancing health and nutrition characteristics. The compositions have a structured lipid content of at least about 80 weight percent and a phytosterol ester content of up to about 20 weight percent, based on the total weight of the health and nutrition promoting composition. The composition significantly reduces total cholesterol and LDL cholesterol without significantly reducing HDL cholesterol, while also reducing adipose tissue of an individual to whom the composition is administered.

38 Claims, No Drawings

U.S. PATENT DOCUMENTS

| | | | |
|---|---|---|---|
| 2002/0048606 A1 | 4/2002 | Zawistowski |
| 2002/0094359 A1 | 7/2002 | Prosise et al. |
| 2003/0054089 A1 | 3/2003 | Prosise et al. |
| 2003/0068425 A1 | 4/2003 | Khare |
| 2003/0175404 A1 | 9/2003 | Nakhasi et al. |
| 2004/0043125 A1 | 3/2004 | Kaimal et al. |
| 2004/0115332 A1 | 6/2004 | Teran et al. |
| 2004/0191391 A1 | 9/2004 | Takeuchi et al. |
| 2004/0219277 A1 | 11/2004 | Wester |
| 2005/0038270 A1 | 2/2005 | Flickinger et al. |
| 2005/0054621 A1 | 3/2005 | Gako-Golan et al. |
| 2005/0261259 A1 | 11/2005 | Burdick et al. |
| 2006/0280856 A1 | 12/2006 | Papathanasopoulos |

OTHER PUBLICATIONS

St-Onge and Jones, "Greater Rise in Fat Oxidation with Medium Chain Triglyceride Consumption Relative to Long Chain Triglyceride is Associated with Lower Initial Body Weight and Greater Loss of Subcutaneous Adipose Tissue," In Press IJO Aug. 13, 2003.

St-Onge, Lamarche, Mauger and Jones, "Consumption of a Functional Oil Rich in Phytosterols and Medium-Chain Triglyceride Oil Improves Plasma Lipid Profiles in Men," Journal of Nutrition, vol. 133, pp. 1815-1820, 2003.

Wester, "Cholesterol-lowering effect of plant sterois", XP-002216851, Eur, J. Lipid Sci, Technol., 2000, pp. 37-44.

PCT Notification of Transmittal of the International Search Report and the Written Opinion of the International Searching Authority, or the Declaration; PCT/US2004/030663; Dated Dec. 22, 2004.

PCT International Search Report; PCT/US2004/030663; Dated Dec. 22, 2004.

PCT Written Opinion of the International Searching Authority; PCT/US2004/030663; Dated Dec. 22, 2004.

Swern, D., 1979, Bailey's Industrial Oil and Fat Products, vol. 1, $4^{th}$ Edition. John Wiley & Sons, New York, pp. 54-55, 210-211.

Swern, D., 1970, Bailey's Industrial Oil and Fat Products vol. 1, $4^{th}$ Edition, John Wiley & Sons, New York, pp. 178-180.

Database FSTA 'Online! International Food Information Service (IFIS), Frankfurt-Main, DE: 2003; St-Onge M P et al; "Consumption of a functional oil rich in phytosterols and medium-chain triglyceride oil improves plasma lipid profiles in men." XP002331082—Database accession No. 2003-00-n0737 abstract—& St-Onge M-P: Journal of Nutrition, vol. 133, No. 6, 2003, pp. 1815-1820, XP002331081 Correspondence (reprint) address, P.J.H. Jones, Sch. of Dietetics & Human Nutr. McGill Univ., Ste-Anne-De-Belleuvue, Que. H9X 3V9, Canada. E-Mail Jonesp(A) MacDonald.McGill.CA.

Database Biosis Online! Biosciences Information Service, Philadelphia, PA, US; Jun. 2003, Bourque Christine et al: "Consumption of an oil composed of medium chain triacyglycerols, phytosterols, and n-3 fatty acids improves cardiovascular risk profile in overweight women." XP002331083 Database accession No. PREV200300363233 abstract.

21 CFR Section 101.83, (Apr. 1, 2002 Edition) pp. 146-149, Anon. 2002.

Heydinger, et al., "Medium Chain Triacylglycerols", Journal of Food Lipids 3, (1996) pp. 251-257.

Swern, D., Bailey'S Industrial Oil and Fat Products, vol. 1, $4^{th}$ Edition, John Wiley & Sons, New York, (1979), pp. 192-196, 210-212.

First Official Communication of European Patent Office in EP 05 724 315.6, dated Feb. 8, 2011.

COMPOSITION WITH HEALTH AND NUTRITION PROMOTING CHARACTERISTICS, CONTAINING INTERESTIFIED LIPIDS AND PHYTOSTEROL, AND RELATED METHODS

CROSS-REFERENCE TO RELATED APPLICATION

This is a continuation-in-part of U.S. application Ser. No. 10/795,843, filed Mar. 8, 2004, and this claims priority from PCT/US2004/030663, international filing date of Sep. 20, 2004 and from PCT/US2005/006745, international filing date of Mar. 2, 2005, each incorporated by reference here into.

BACKGROUND OF THE INVENTION

1. Field of the Invention

This invention generally relates to compositions of structured lipids and phytosterol esters. These compositions are especially suitable for use as components having health and nutrition promotion characteristics. More particularly, the invention relates to structured lipids for use as edible oils in combination with phytosterol esters in a variety of applications for promoting health and nutrition enhancement for those applications, such as in products for consumption and/or use by living beings, especially humans.

2. Description of Related Art

Vegetable-based edible oil compositions long have been used in baking, frying and food dressing applications. Edible oil products provide taste, nutrition and anti-stick properties for any number of pan cooking, baking, dressing or similar types of uses and applications. Edible oil products of this general type include liquid oils, cooking oils, margarines, whipped spreads, tub margarines, shortenings, oils, sprayable compositions, salad dressings and the like. Edible oils also can be included in compositions administered to individuals in compositions that are not necessarily mainstream food products. Some can be directed to fine tuning nutritional input or addressing metabolism objectives. Traditional edible oil products, including those of the long chain variety, have been used in these types of applications.

In the health, nutrition and metabolism art, publications suggest the usefulness of phytosterols in oil-based compositions. References which are in this general field include St-Onge, et al., "Consumption of a Functional Oil Rich in Phytosterols and Medium-Chain Triglyceride Oil Improves Plasma Lipid Profiles In Men," *American Society for Nutritional Sciences*, 0022-3166/03, (2003), *Journal of Nutrition*, Volume 133, pages 1815-1820, (2003) reports a study evaluating the effects of a combination of medium chain triglyceride oil, phytosterols and flaxseed oil on plasma lipid concentrations and LDL particle size. Another article discussing plant sterols or phytosterols is St-Onge, et al., "Phytosterols and Human Limpid Metabolism: Efficacy, Safety and Novel Foods," *Lipids*, Volume 38, No. 4, pages 367-375, (April, 2003). This article reports on studies regarding cholesterol-lowering efficacy of plant sterols with a view toward greater use of phytosterols in heart health promotion.

Medium chain triglyceride (MCT) edible oils are known in the art including Seiden U.S. Pat. No. 5,288,512, Bertoli et al. U.S. Pat. No. 5,395,629, Hidaka U.S. Pat. No. 5,503,855 Takeuchi U.S. Patent Publication No. 2002/0001660, and Heydinger and Nakhasi, "Medium Chain Triacylglycerols, *Journal of Food Lipids*, Volume 3, pages 251-257 (1996). Additional articles concerning MCT art include the following. St-Onge, et al., "Medium-Chain Triglycerides Increase Energy Expenditure and Decrease Adiposity in Overweight Men," *Obesity Research*, Volume 11, No. 3, (March, 2003) indicates that upper body adipose tissue in this study decreased using a functional oil blend of medium chain triglyceride oil, canola oil, flaxseed oil, coconut oil, and unesterified stanol/sterol mixture. St-Onge et al., "Greater Rise in Fat Oxidation With Medium Chain Triglyceride Consumption Relative to Long Chain Triglyceride is Associated With Lower Initial Body Weight and Greater Loss of Subcutaneous Adipose Tissue," *International Journal of Obesity*, Volume 27, Pages 95-102 (2003) reports on a study to the effect that body weight decreased with medium chain triglyceride consumption when compared with long chain triglyceride consumption. These references, and each of the publications and patents noted throughout herein, are incorporated by reference hereinto.

Publications such as these define these medium chain triglyceride or medium chain triacylglycerol (MCT) compounds as being a class of lipids of glycerol ester fatty acids. MCTs are esters of glycerol with medium chain fatty acids of 6 to 12 carbon chain lengths. Sources typically are lauric oils. Coconut and palm kernel oils contain significant quantities of C8 (caprylic) and C10 (capric) chains. Often, isolated fractions of C8 and C10 acids contain small amounts of C6 and C12 acids as well. Generally, MCT esters are saturated. Accordingly, the primary components of MCT edible oils have C8:0 and C10:0 fatty acid chains.

References of Forbes Medi-Tech Inc also discuss phytosterol compositions. Stewart et al. U.S. Pat. No. 6,087,353 describes phytosterol compositions which are esterified and subsequently hydrogenated. These are said to be suitable for use alone or for incorporation into foods, beverages, pharmaceuticals, nutraceuticals, and the like. Other references discussing phytosterol compositions and their effects on cholesterol include the following. Nguyen T T, Dale L C, von Bergmann K, Croghan I T, Cholesterol-lowering Effect of Stanol Ester in a US Population of Mildly Hypercholesterolemic Men and Women: a Randomized Controlled Trial, *Mayo Clin Proc.*, December, 1999; 74(12):1198-206, compares the effects of stanol ester margarine-like spreads showing decreases in cholesterol levels in human subjects. Hallikainen M A, Sarkkinen E S, Uusitupa M I, Plant Stanol Esters Affect Serum Cholesterol Concentrations of Hypercholesterolemic Men and Women in a Dose-dependent Manner, *J Nutr.*, April 2000; 130(4):767-76, administered doses of plant stanol esters added to a margarine. Deceereases in total cholesterol and LDL cholesterol were indicated, such leveling off with higher doses.

St-Onge M P, Lamarche B, Mauger J F, Jones P J, Consumption of a Functional Oil Rich in Phytosterols and Medium-chain Triglyceride Oil Improves Plasma Lipid Profiles in Men. *J Nutr.*, June 2003; 133(6):1815-20, evaluated the effects of a combination of MCT oil, phytosterol and flaxseed oil blend on plasma lipid concentration and LDL particle size.

Zerawistowski et al., International Publication No. WO 01/91587 describes oil compositions comprising short, medium and long chain triglycerides and the use thereof in reducing weight gain. Zawistowski et al., also discusses phytosterols, which incorporates phytostanols as noted therein. These phytochemicals are presently believed to have an ability to decrease serum cholesterol levels when fed to a number of mammalian species, including humans. Zawistowski et al. indicates that the relationship between cholesterol and phytosterol is apparently due in part to similarities in the respective cholesterol and phytosterol chemical structures. The mechanism set forth in references such as these is that phytosterols displace cholesterol from the micellar phase to reduce its absorption or compete with cholesterol in its absorption process. Esterification of triglycerides is generally referenced in Zawistowki et al., including referring to interesterifying short, medium and long chain triglycerides for forming described chain residues.

Interesterification is a known reaction of triacylglycerol structures whereby individual fatty acid structures at positions of the triglyceride being interesterified are interchanged on the glycerol moiety. This is at times referred to or recognized as a randomization wherein fatty acid moieties from one glycerol component of a triacylglycerol are exchanged with those of a glycerol component of another triacylglycerol. This results in triacylglycerol structures which have interchanged fatty acid moieties that vary from glycerol structure to glycerol structure. Art in this area includes Pelloso et al. U.S. Pat. No. 5,434,278, Doucet U.S. Pat. No. 5,908,655, Cherwin et al. U.S. Pat. No. 6,124,486 and Liu et al. U.S. Pat. No. 6,238,926.

The art of interesterification has developed to form, for example, triglyceride compositions which provide certain melt profiles that can be of interest in certain applications. Generally these are recognized herein as "structured lipids" in order to help distinguish the interesterified products from other products which are physical blends of the same components but that have not been subjected to interesterification.

Heretofore, it has not been appreciated that the combination of interesterification technology and MCT technology and phytosterol technology would be especially advantageously applied to the task of improving health, nutrition and metabolism promoting compositions having substantial edible oil content. An especially important problem in this regard, which is addressed by interesterified components according to the invention, is to provide a composition that has health, nutrition and improved metabolism promoting characteristics while simultaneously exhibiting very acceptable properties for combining with and/or adding into products for ingestion by and/or treatment of individuals. Most especially, it has been found that the compositions of this invention are substantially equal, or improved, substitutes for conventional edible oils used in making and/or formulating food products.

SUMMARY OF THE INVENTION

In accordance with the present invention, products are provided which can be used in place of, or in combination with, conventional edible oil products such as domestic oils or tropical oils. These products are compositions of specially constructed edible oils in combination with a phytosterol ester component. These products have as a principal component a structured lipid which is a product of the interesterification of an edible domestic oil triglyceride and a medium chain triglyceride. These structured lipids are combined with phytosterol esters into so-called healthy oil compositions. When desired, these compositions can be formulated with components of a type typically included within compositions for a selected intended use.

The structured lipid and phytosterol compositions have the ability to function well in food systems, especially for baking, sauteing, stir-frying and as an oil component of a dressing or other product that is used and/or stored at room temperature or refrigerated temperatures. By virtue of this good functionality of these compositions, the health, nutritional and positive metabolic benefits of phytosterols and of medium chain triacylglycerols are provided in traditional products which are likely to be more readily consumed by those who can benefit from the health attributes of the components.

A general aspect or object of the present invention is to provide compositions which combine structured lipids with phytosterol esters to provide compositions suitable for health and nutrition promotion in individuals.

An aspect or object of the present invention is that it provides medium chain triglycerides which have been modified by longer chain edible oils, for the purpose of enhancing health and/or nutrition of products within which they are combined together with phytosterol esters, including when compared with compositions having blends of the same MCT and longer chain components that are not subjected to interesterification.

Another aspect or object of this invention is that it provides structured lipids displaying a solids fat content which is substantially liquid at 10° C., which solids fat content is very appropriate for combination with phytosterol esters into compositions which can be liquid and clear at room temperature and below.

Another aspect or object of the present invention is providing a process for accomplishing randomized interesterification of medium chain edible oils with long chain edible oils and the use of the resulting product in compositions for health and/or nutrition promotion in a form which facilitates consumption for reaping the benefits of the composition in humans or other mammals.

Another aspect or object of this invention is that it provides an improved composition and method which combines the virtues of MCT technology and phytosterol technology with the special improvement of interesterification for enhancing compatibility and shelf stability of compositions which exhibit excellent suitability for use in food products and preparations.

Another aspect or object of the present invention is to address obesity concerns by improving the quality of lipid intake, especially by individuals exhibiting overweight or obese characteristics by ingesting structured lipid and phytosterol compositions.

Another aspect or object of the present invention is to provide lipid products that achieve total cholesterol reduction and LDL cholesterol reduction to an extent which is greater than that achieved by extra virgin olive oil, recognized as an especially valuable lipid for cholesterol reduction.

Another aspect or object of the present invention is to provide lipid compositions which, when used in place of other edible oils and/or fats, is a tool in addressing obesity and dyslipidemia problems.

Other aspects, objects and advantageous of the present invention will be understood from the following description according to the preferred embodiments of the present invention, specifically including stated and unstated combinations of the various features which are described herein.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The present invention is directed toward structured lipids produced from medium chain triglycerides. Medium chain triglycerides usually are produced commercially by splitting and distilling fatty acids from coconut or palm kernel oils. Production includes esterification with glycerine to form a triglyceride having fatty acid chain lengths of from C6 to C12. These known edible oils typically contain 50 to 80 weight percent of C8 caprylic fatty acids and between about 20 and about 50 weight percent of CIO capric fatty acids. Minor levels, typically between about 1 and about 2 weight percent, of either or both of C6 caproic fatty acids and C12 lauric fatty acids can be present in some such products.

Known medium chain triglyceride, or "MCT," products include some NEOBEE® products such as NEOBEE® M-5 (trademark and product of Stepan Company), ALDO MCT (trademark and product of Lonza, Inc.), CAPTEX® 300 (trademark and product of Abitec Corp.), and MIGLYOL® 812 (trademark and product of Clionova, Inc.). Traul et al., "Review Of The Toxicologic Properties Of Medium-Chain Triglyceride", *Food and Chemical Toxicology*, 38, pages 79-98 (2000) indicate that MCTs are essentially non-toxic in acute toxicity tests conducted in several species of animals. This article also indicates that MCTs exhibit virtually no ocular or dermal irritant potential, even with prolonged eye or skin exposure. This article also indicates that MCTs exhibit no capacity for hypersensitivity induction. According to this publication, the safety of MCTs in human dietary consumption has been indicated up to levels of 1 gram per kilogram of body weight.

Another publication indicates that MCTs result in lower fat deposition when compared with long chain triglycerides. This is noted in Ingale et al., "Dietary Energy Value of Medium-Chain Triglycerides", *Journal of Food Science*, Volume 64, No. 6, pages 960-963 (1999). Conclusions reached in this article state that differences in energy utilization show that increments of heat associated with the metabolism of MCTs appears to be about 16% higher as compared to long chain triglycerides. With this in mind, the calculated mean net caloric energy value for MCTs used in diets is on the order or 6.8 kcal/g. This is lower than typical LCTs (9.0 kcal/g). According to the publication, substituting MCTs for LCTs as the source of fat in diets show reduced weight gain and reduced fat deposition in laboratory animals and humans. This is said to be due to the lower gross energy density of an efficient utilization of energy from MCTs.

From this information, medium chain triglycerides are indicated as having dietary advantages at least from the point of view of fat deposition. Medium chain triglycerides also are indicated by art such as this as being suitable for use in the context of human food applications. MCTs however have relatively low smoke points, making them less than satisfactory for use in food applications.

Interesterification of these MCTs according to the invention includes charging them to an interesterification location or vessel as part of the charge for forming the structured lipid. Broadly, MCTs can comprise between about 15 and about 75 weight percent of the total structured lipid charge components. Typically, MCTs comprise between about 25 and about 75 weight percent of the structured lipid charge. Generally, the charged quantities of interesterification reactants correspond closely to the respective weight percents in the interesterified structured lipid. Preferably, the quantity of MCTs is between about 30 at about 60 weight percent, most preferably between about 35 and about 55 weight percent.

Also part of the charge for forming the structured lipids are so-called domestic oils. Domestic oils for the interesterification according to the invention include soybean oil, corn oil, cottonseed oil, canola oil, safflower oil, sunflower oil, peanut oil, olive oil, oil from grain plants, and identity preserved oils such as identity preserved canola oil and the like. Whichever edible oil is chosen, it will be a liquid oil. Hydrogenation typically need not be carried out. Oils of these types are well recognized as so-called long chain lipids. Chain lengths of these oils generally lie between C16 and C22, as will be generally appreciated in the art.

The charge of such domestic oil to the interesterification location or vessel broadly can be between about 15 and about 85 weight percent of the charge into the interesterification reaction vessel. Typically, the oil comprises between about 25 and about 75 weight percent of the charge, and substantially the same level of long chain component is in the interesterified structured lipid. Preferably, this amount is between about 40 and about 70 weight percent, most preferably between about 45 and about 65 weight percent, based upon the weight of the charge or interesterified structured lipid.

With further reference to the domestic oils having chain lengths longer than the MCT reactant, advantageously they are preferably substantially unsaturated oils such as soybean, corn, cottonseed and canola, which are well known in the art as liquid oil commodities. Certain specialty oils also are encompassed within the preferred domestic oils. These include identity preserved canola oils and refined, bleached and deodorized high stable oils. Included is naturally high stable canola oil such as NATREON oil (trademark, available from Dow Agro Sciences, Canbra Foods), which is naturally higher in monounsatarated fats and in oleic fatty acid and lower in linolenic fatty acid. In this regard, Sornyk et al U.S. Pat. No. 5,965,755 and Lanuza et al. U.S. Pat. No. 6,169,190 are noted and incorporated by reference.

The chemical interesterification used in making the structured lipids of the compositions of the invention involves charging the reactants into an interesterification reactor vessel. Such vessels have means for heating the reactants during agitation and under reduced pressure or vacuum conditions. The reaction is carried out in the presence of a suitable interesterification catalyst and typically proceeds rapidly to completion or substantial completion. Typically, the interesterification is a reaction to or toward complete randomization, which would equate to a degree of interesterification of 100% of the fatty acyl chains.

Interesterification catalysts include metal alkoxides, alkali metals, alkali metal alloys, and metal hydroxides. Alkoxides include alkali metal alkoxides, such as sodium methoxide, sodium ethoxide, potassium methoxide and potassium ethoxide. Alkali metals include sodium. Alkali metal alloys include sodium/potassium alloy, and metal hydroxides include alkali metal hydroxides such as sodium hydroxide and potassium hydroxide.

Once the interesterification has proceeded to form the desired structured lipid, steps can be taken to modify the conditions away from reaction conditions. This can include inactivating the catalyst, reducing the temperature, reducing the vacuum applied, ceasing agitation, or any combination of these changes. Means for accomplishing these changes will be appreciated by those skilled in the art.

Reaction temperatures range between about 80° C. and about 100° C. (about 160° F. to about 212° F.). A most suitable temperature at which to carry out the interesterification within the reaction vessel is approximately midway within this range. Vacuum conditions within the vessel range between about 5 mbar and about 100 mbar (between about 4 mm Hg and about 75 mm Hg). Preferably, the level is within the lower portion of this range, or less than about 40 mbar (about 30 mm Hg), most preferably at or below about 26.7 mbar (about 20 mm Hg).

Reaction time will range between about 30 minutes and about 2 hours. An especially suitable reaction time is about 45 minutes. This reaction time can be controlled, for example, by timed neutralization of the catalyst. Neutralization for a catalyst such as sodium methoxide can be accomplished with 0.7 weight percent of citric acid solution of 42% strength.

The interesterified structured lipid can be treated to remove any residual soaps and/or to remove all the color bodies if needed. These include filter aids and silica sources such as TRISYL® S-615 (trademark, available from W. R. Grace & Co.) used for the refining of vegetable oil. Color removal can be with a bleaching earth or the like. The structured lipid also typically will be subjected to deodorization in accordance with approaches generally known in the art.

In preparing the products according to the invention, the interesterified structured lipid is combined with one or more phytosterol esters to form a composition which can be used directly as an edible oil product, or also be combined with other components to make up the desired final product, as will be generally appreciated by those skilled in the art. For example, this can include combining the composition with other food components in recipes for consumable foods and the like.

Compositions according to the invention include the structured lipid at levels between about 80 and about 96 weight percent, based upon the total weight of the product. Typically the structured lipid will be present at between about 92 and about 95 weight percent. The phytosterol component will be included at levels between about 4 and about 20 weight percent, based on the total weight of the composition. Typically the phytosterol will be present at between about 5 and about 8 weight percent.

With further reference to the phytosterols that serve as the basis for the phytosterol ester components that are combined with interesterified structured lipid according to the invention, specific details concerning phytosterols can be found in U.S. Pat. No. 6,117,475, No. 6,139,897, No. 6,277,431, No. 6,562,395 and No. 6,713,118, International Publications No. WO 01/13733, No. WO 01/32029 and No. WO 01/91587. Specific details concerning phytosterol esters and microparticles of phytosterol esters are found in U.S. Pat. No. 6,087,353 and U.S. Patent Application Publication No. 2002/0048606. As noted previously, each of these patents and patent publications is incorporated by reference hereinto.

The term "phytosterols" when referring to the components used in the compositions according to the present invention encompass phytosterols and/or phytostanols or derivatives of these types of compounds. It is recognized that the presence of the sterol component is useful in lowering serum cholesterol and serum triglyceride levels, as well as enhancing overall dietary efficacy. It is generally accepted, but not with certainty, that this can be explained by similarities between their respective chemical structures. By this explanation, the phytosterol displaces cholesterol from the micellar phase, thereby reducing cholesterol absorption and/or competing with receptor and/or carrier sites in the cholesterol absorption process.

Examples of compounds which fall within a meaning of "phytosterol" include sitosterol, campesterol, stigmasterol, brassicasterol, demosterol, chalinosterol, poriferasterol, coioanasterol, and natural or synthesized forms or derivatives, including isomers. Also included are compounds identified by the term phytostanol, including saturated or hydrogenated phytosterols and all natural or synthesized forms and derivatives, including the isomers. It will be appreciated that these components can be modified, such as adding side chains and also fall within the perview of the term phytosterol.

Phytosterols are typically attained from natural sources, most typically from the processing of plant oils. Sources include vegetable oils, which include corn oil, wheat germ oil, soy extract, rice extract, rice bran, canola oil and sesame oil. Other sources can include tall oil pitch or soap such as those which are byproducts of the forestry industry.

Phytosterol esters are available from public sources, including from Forbes Medi-Tech, Inc. An example is PHYTROL®, a registered trademark of Forbes Medi-Tech, Inc. Compositions are sold under this brand name as cholesterol lowering agents. A typical such composition is composed of plant sterols and stanols having 14.5% campesterol, 2.4% campostanol, 50.9% beta-sitosterol, and 18.9% sitostanol. The PHYTROL® product is a fine crystalline waxy powder. Its particle size characteristic is such that greater than 80% of the particles pass through a 0.8 mm sive and greater than 98% of the particles pass through a 2.0 mm sive. PHYTROL® phytosterol compositions comprise from 38 to 79 weight percent sitosterol, based on the total weight of the anhydrous composition, 4 to 25 weight percent of campesterol, 6 to 18 weight percent sitostanol, and 0 to 14 weight percent campostanol. At least 97 weight percent of the components are in the form of a sterolester, and no more than 3 weight percent are free sterols. An exemplary sterolester in this regard is a phyto-S-sterol-10 ester. Such has a softening point of between 15° C. and 30° C. and is substantially insoluble in water at 25° C. Such a sterolester is liquid above 40° C.

With more particular reference to the phytosterol ester component, it is preferred that the quantity of stanol structures included in this component be minimized. The stanol structure is associated with hydrogenization is associated with trans-isomer structures, which have been the subject of negative health concerns. In addition, excessive hydrogenization detrimentally affects clarity of the compositions. Typically, the stanol or phytostanol content in the phytosterol ester components according to the invention will be no greater than about 20 weight percent, based upon the total weight of the phytosterol ester component. Preferably, the amount of stanol or phytostanol compounds within the phytosterol ester component is not greater than about 15 weight percent.

In proceeding with methods according to the invention, between about 90 and about 96 weight percent of the interesterified structured lipid described herein is blended with between about 4 and about 10 percent of a phytosterol ester component, both based upon the total weight of the composition. In a preferred arrangement, the structured lipid is prepared by an interesterification reaction as discussed herein of approximately equal weight percentages of a medium chain triglyceride and of a long chain domestic oil, each as generally discussed herein.

In keeping with the methods, these compositions then are formulated into food products so that adequate levels of phytosterols are delivered into the body in order to reduce total cholesterol adsorption. In addition, the MCT structure fosters their oil metabolism through the hepatic system rather than through the lymphatic system, leading to reduced adipose tissue deposition for these oil products when compared with products incorporating similar quantities of other oils. The compositions also are intended to increase components of energy expenditure and substrate oxidation.

This structured lipid combined with phytosterol esters as discussed herein provide an excellent composition for edible oil products having good clarity, physical properties for such uses, and low trans-isomer levels. This composition provides a healthy oil that delivers salad oil, frying and baking functionality while serving as an adjunct to lower LDL cholesterol levels and minimizing adipose tissue deposition. LDL cholesterol levels are reduced to a statistically significant degree when compared with diets not including same, and are significantly reduced when compared with "gold standard" oils for health characteristics such as extra virgin olive oil. Reductions in LDL are at least about 10 percent, preferably at least about 15 percent and most preferably at least about 20 percent. Reductions in total cholesterol are at least about 8 percent, preferably at least about 12 percent, most preferably at least about 15 percent. This is accomplished without any statistically significant reduction in HDL cholesterol and shows less reduction of HDL, in a directional sense, than extra virgin olive oil.

Administration of the structured lipid-based, phytosterol ester-containing oil composition according to the invention can be made at advantageous levels when included within a monitored diet. Administration doses should be at least about 0.4 grams of the oil composition per kilogram of body weight per day. Typically, the dose level will be not more than about 2 grams/kg/day. A typical range can be between about 0.6 and about 1 gram of this oil per kilogram of body weight per day. In an exemplary monitored diet, 40% of the total energy (approximated by calories) in the diet originate from fat, 45% of the energy from carbohydrates, and 15% of the energy from protein sources. Of the fat source, 75% can be provided by the structured lipid composition. Thus, a monitored diet designed for lowering LDL cholesterol, raising HDL cholesterol and/or raising the HDL/LDL cholesterol ratio level in this example achieves 28% of its energy from the structured lipid-based, phytosterol ester-containing compositions according to the invention.

On a body mass basis, this type of monitored diet expends energy sources at a rate of between about 2200 and about 2500 calories per day. The structured lipid-based, phytosterol ester-containing oil compositions according to the invention exhibit 8.4 kilocalories per gram of fat, whereas a typical edible oil such as refined, bleached and deodorized canola oil exhibits 9 kilocalories per gram of fat.

Examples now are provided in order to illustrate the concepts of the invention with a certain degree of specificity. Brookfield viscosity measurements referenced herein are measured at 20° C. with a No. 4 spindle at 50 rpm on a Brookfield Viscometer.

EXAMPLE 1

A batch reaction was carried out within a reactor vessel having heating means, agitation means and pressure reduction capabilities. The reactant charge was 50% by weight of a medium chain triglyceride (NEOBEE® 1053) and 50% by weight of identity preserved canola oil. A sodium methoxide catalyst (95% pure) was added at 0.15 percent by weight of the edible oil reactant charge. The interesterification reaction was allowed to proceed for 45 minutes at a temperature of 90° C. and a pressure of 25.3 mbar (19 mm Hg). At the end of the reaction time, neutralization was carried out with 0.7% by weight of citric acid solution of 42% strength by weight.

The thus-formed interesterified structured lipid was treated with 1% by weight TRISYL® S-615 plus 1% by weight of a filter aid. Mixing proceeded for about 8 minutes at 90-94° C., followed by filtration. This was observed to have removed all of the soap residue. The structured lipid also was bleached with 0.5% of bleaching earth and 0.5% of a filter aid in order to ensure that all color bodies were removed.

Deodorization was carried out as follows. The structured lipid was subjected to a temperature of about 230° C. under a vacuum of 2.66 mbar (2 mm Hg). Steam was introduced at the rate of 0.4 volume percent of steam per hour. Deodorization treatment time was four hours.

The structured lipid was analyzed and found to have the following characteristics. No soap was detected. The smoke point was 210° C. (410° F.). The viscosity was measured with a Brookfield viscometer at 20° C., using the No. 4 spindle at 50 rpm. The viscosity reading for this structured lipid was 22 centipoise. The same MCT and identity preserved canola oil in the same proportions were made up into a physical blend. The Brookfield viscosity at 20° C., with spindle No. 4 at 50 rpm, was 40 centipoise, and the smoke point was 154.4° C. (310° F.). The canola oil, prior to blending, had a viscosity of 68 centipoise measured in the same manner.

Good product stability was indicated by a free fatty acids value of 0.03. The peroxide value (PV) was 0.2. The oxidative stability index (OSI) was 15.5 hours at 110° C. The solids fat content (SFC) at 10° C. was 0.32, indicating that the structured lipid was liquid at this temperature. The Anisidine Value (AV) was comfortably low, at 0.85. The color measurement according to PFX880 5¼ was 7.5 Y/1.3 R.

The peroxide value (PV) is determined in accordance with method No. Cd8-53 from the publication *Official Methods and Recommended Practices of the AOCS*, Fifth Edition (2002). Also found in this publication are method No. Ca5a-40 for free fatty acid (FFA) determination, method No. Cd18-90 for Anisdine Value (AV) determination, and method No. Cd12b-92 for Oxidative Stability Index (OSI) determination.

The structured lipid was blended with phytosterol ester to prepare the structured lipid phytosterol composition of this Example, such having a sterol ester content of 6 weight percent. Various food products were prepared using this structured lipid phytosterol composition and also using control oil sources. Comparative analyses and sensory tests were conducted. The results indicate that there were no significant differences between food products prepared with the structured lipid of this Example when compared with the control oil. In some instances noted herein, the structured lipid composition according to this Example gave results that were more favorable to a statistically significant degree.

Provided in Table I are oil quality attributes which are the results of tests reporting basic quality attributes of the refined, bleached and deodorized canola oil and of the structured lipid phytosterol ester composition according to this Example.

TABLE I

| Analytical Test | RBD Canola Oil | Structured Lipid-Sterol Oil |
|---|---|---|
| OSI | 6-7 hrs. | 16.0 hrs. |
| Smoke Pt. | 475° F. | 410° F. |
| Color-(5¼) | 7.0Y/0.7R | 7.5Y/1.3R |
| FFA (%) | 0.03 | 0.03 |
| PV(meq/kg) | 0.8 | 0.8 |
| Iodine Value | 100-115 | 59.1 |
| Viscosity | 68 cp | 22 cp |
| % Trans | 0.36% | 0.36% |
| Sterol Ester | 0.81% | 6.00% |
| Campsterol | 269 mg/100 g | 403.5 mg/100 g |
| Stigmasterol | 14.3 mg/100 g | 57.3 mg/100 mg |
| Beta Sitisterol | 528.0 mg/100 g | 2992.5 mg/100 g |

These data of Table I provide certain information of interest. The oxidative stability index (OSI) for the canola oil was only 6-7 hours, whereas that for the structured lipid composition of this Example was 16 hours. The higher OSI value indicates that the structured lipid-based phytosterol-containing oil remains stable and clear for a greater number of hours than the control oil. This indicates a longer shelf stability than the control oil. While the smoke point of the structured lipid of this Example is lower than that of the control canola oil, the level of 410° F. (210° C.) is acceptable for pan frying applications other than deep frying. In addition, this smoke point is higher than the smoke point of a composition according to this Example but which is a blend and does not subject the lipid components to interesterification.

The iodine value (IV) is significantly lower for the structured lipid-based oil than for the canola oil control. The IV indicates the degree of unsaturation, even though the structured lipid oil based composition is liquid at room temperature. This and other physical properties indicate that the structured lipid-based composition is liquid, and there is no significant precipitation, including if stored under refrigerated temperatures for reasonable lengths of time. Crystallization will be resisted for a much longer time, under refrigeration, than for the canola oil control. The oil remains a clear liquid for a longer time than oils having quality attributes along the lines of the canola oil in Table I.

The viscosity data indicate a substantially lower viscosity for the structured lipid-based phytosterol-containing oil, indicating that this oil is lighter in weight or consistency than is the canola oil. The percent of trans-isomer is the same for the structured lipid oil as it is for canola oil. The level of 0.36% generally corresponds to the natural level of trans-isomers within canola oil and indicates that the structured lipid-based oil also enjoys this advantageously low trans-isomer percentage. The substantially higher quantity of sterol ester in the structured lipid-based oil is consistent with the phytosterol added thereto. The 0.81% sterol ester in the canola oil control represents the natural level within the canola oil.

Table I also shows levels of the major phytosterols present in each of the structured lipid-based oil and in the canola oil. It is noted that the beta-sitisterol content which is present in a 5-fold greater amount in the structured lipid-based oil over the canola oil is the most important phytosterol for LDL reduction which is found in these types of phytosterol components.

Shelf Life Study

The structured lipid-based phytosterol-containing oil composition of this Example 1 was subjected to a shelf life study at three different temperatures. Data were generated and are reported in Table II. The ambient storage temperature was within an open room having typical heating, ventilation and air conditioning cycles averaging on the order of 70° F. (about 21° C.). The 70° F. (21° C.) and 100° F. (37.8° C.) storage temperatures were within closed spaces with closely monitored temperatures. The storage temperature of 100° F. is considered to be an accelerated test for shelf storage evaluation.

TABLE II

| Storage Time | Storage Temp. | Peroxide Value (Meq/Kg) | Free Fatty Acids (wt. %) | Anisidine Value | OSL (hours) |
| --- | --- | --- | --- | --- | --- |
| Time Zero | — | 0.2 | 0.07 | 1.28 | 16 |
| 1 Month | Ambient | 0.2 | 0.07 | 0.64 | 14.62 |
|  | 70° F. | 0.2 | 0.07 | 0.67 | 13.68 |
|  | 100° F. | 1.8 | 0.07 | 0.69 | 14.47 |
| 3 Months | Ambient | 1.2 | 0.07 | 0.64 | 13.90 |
|  | 70° F. | 1.2 | 0.07 | 0.66 | 14.03 |
|  | 100° F. | 3.0 | 0.08 | 1.35 | 12.35 |
| 6 Months | Ambient | 3.6 | 0.07 | 0.87 | 12.37 |
|  | 70° F. | 3.9 | 0.07 | 0.94 | 11.78 |
|  | 100° F. | 4.3 | 0.08 | 1.85 | 11.23 |
| 7 Months | Ambient | 4.0 | 0.07 | 0.74 | 12.35 |
|  | 70° F. | 4.4 | 0.07 | 1.05 | 12.65 |
|  | 100° F. | 4.2 | 0.08 | 2.01 | 11.67 |

The structured lipid oil was blended with PHYTROL® phytosterol at a ratio of 94% structured lipid and 6% phytosterol. The Table II data show a very consistent free fatty acid (FFA) weight percent. This lower free fatty acid content indicates that the structured lipid-based phytosterol-containing composition has not broken down over the seven month period, indicating that the triglycerides are intact. An anisidine value (AV) of about 2 or lower, or even 3 or lower, indicates very low beta oxidation or secondary oxidation. When the AV exceeds 3, this is an indication that the oil is beginning to become oxidized and free fatty acids have formed, which can eventually move toward rancidity.

The peroxide value (PV) is an alternative manner of judging shelf life. Bottled edible oils are generally appreciated as having acceptable shelf properties when the PV is no greater than or equal to about 8 meq/kg.

The oxidative stability index (OSI) shows that the advantageous 16 hour value for the fresh structured lipid-based oil, while reduced somewhat after seven months, is nevertheless still approximately twice that of the fresh canola oil (see Table I).

Comparative Sensory Testing

Comparative testing of food products incorporating the structured lipid phytosterol ester composition of this Example 1 shows the suitability of using such compositions in products which will successfully deliver the phytosterols (in greater quantities as noted in Example 15) without detracting from the sensory attributes of the food products.

Cake Evaluation Study

Identical cake batters were prepared with the exception of the oil component. NUTRA-CLEAR OIL® canola-based oil, available from Bunge Oils, was the control oil in this cake evaluation study. In this study, as well as in all of the other studies of this Example, a so-called "healthy oil" was used. This is the structured lipid-based, phytosterol ester-containing edible oil composition of this Example. In making up the respective yellow cake batters and baked cakes, subjective and objective test results show no significant differences. More specifically, for each of the control and healthy oils, the respective values were 0.909 and 0.918 for specific gravity, 10,260 and 10,180 centipoise for the viscosity of the batter, 68° F. (20° C.) batter temperature for both, smooth batter appearance for both, cake volume of 1235 cc for both, firm texture for both, with a "moist" comment regarding performance for the control and a "gummy" performance comment for the healthy oil. The moisture contents for the control oil and healthy oil were 41.21% and 41.86%, respectively, and the water activities were 0.927 and 0.942, respectively.

A sample of each baked cake was subjected to analyzation within a TA-XT2 Texture Analyzer manufactured by Stable Micro Systems, of Goldalming, Surrey, England. This analyzer was set at the following parameters used to analyze the yellow cakes for texture: 3.00 mm/s pretest speed, 1.70 mm/s test speed, 1.70 mm/s post-test speed, 1.0% rupture test distance, 70% distance, 100 grams force, a time of 3.00 seconds, a count of 5, and a 25 kg load cell. The control analyzed at 2919.57 grams of force, and the healthy oil analyzed at 2741.46 grams of force. This is a measure of the grams of force required to depress the cake sample at a given rate as set on the Texture Analyzer. These objectively measured values of texture gave the conclusion of no significant difference between the cakes made with the two different types of oils.

In addition, these yellow cakes were subjected to sensory evaluation according to the triangle technique as specified in *Sensory Evaluation Techniques*, 3$^{rd}$ Edition, CRC Press, page 369 (1999). A panel of 40 individuals was presented with yellow cake samples in a blind taste test. Two of the samples were either the control cake or the healthy oil cake, with the third sample being of the other cake. Each participant was requested to select the sample which was different from the other two in sensory attributes. 18 out of the 40 participants correctly identified the different cake sample, which indicates no significant sensory difference between the two cakes according to these triangle sensory test results of the control oil containing cake and of the healthy oil containing cake. This is at a 95% confidence level.

Muffin Evaluation Study

Muffins were prepared using consumer-type muffin mixes that require oil in the make-up instructions. In one test batter, the NUTRA CLEAR OIL® canola oil product was used as the control, and the structured lipid phytosterol ester composition of this Example was the so-called healthy oil. The respective values of the control oil to the healthy oil were as follows: specific gravity, 0.943 and 0.952; viscosity 22,040 cps and 20,800 cps; moisture 35.70% and 39.80%; and water activity 0.943 and 0.952, respectively. In each case, the batter temperature was 68° F. (20° C.) and the batter appearance was smooth. Each was judged to have good texture and was moist. Informal sensory evaluations indicated no flavor differences, although an appearance difference was noted in that the control muffins had a peaked appearance, rather than a rounded top appearance of the healthy oil muffins. Overall, no significant differences were found between the two muffin products.

Waffle Evaluation Study

Waffles were made using BUNGE® pancake mix having a specified amount of oil added to the batter to produce Belgian style waffles. Both the control oil and the healthy oil produced similar waffles. There were no differences in batter viscosity or specific gravity. Informal sensory evaluations showed no appearance or flavor differences. Each had a nice golden brown color and a clean flavor.

Sautéed Vegetable Evaluation Study

In this study, the control canola based oil product and the healthy oil product were evaluated, as was a third oil, namely Bertolli olive oil as sold to retail consumers. Vegetables were stir fried in each oil and evaluated for flavor, color and functionality attributes. The healthy oil exhibited some smoking and foaming. Sensory evaluations showed no differences in appearance. It was noted that the vegetables sauteed in the healthy oil exhibited a "cleaner" flavor than the other oils, which enhanced the flavors of the vegetables.

Pan-Fried Chicken Evaluation Study

Long chicken strips were placed into a tempura-type batter and fried in the control canola oil and the healthy oil. As with the vegetable evaluation, some smoking and foaming was observed when pan frying in the healthy oil. Informal sensory evaluations showed no differences in appearance. Taste testing showed that a "fishy" taste was noted in the samples fried in the control oil, which taste was considered objectionable. The chicken fried in the healthy oil was very desirable with a very "clean" flavor and no aftertaste.

Salad Dressing Evaluation Study

Vinegar and oil salad dressings were prepared using a 3:1 ratio of 3 parts oil to 1 part red wine vinegar. One sample used the NUTRA-CLEAR OIL® canola oil, and the other used the healthy oil composition of this Example. Both oils produced dressings which were very similar in appearance. Sensory evaluations showed that the canola oil dressing seemed bland, while the healthy oil dressing seemed to have more bitter vinegar flavor, which is judged to be a positive flavor attribute.

A triangle sensory test was conducted in substantially the same manner as the yellow cake triangle sensory testing reported above. 15 of 33 respondents correctly discerned which salad dressing was different. This indicates that there was no significant difference in sensory attributes between the two salad dressings, at a 95% confidence level.

Olive Oil Salad Dressing Evaluation

Salad dressings were made up as in the salad dressing evaluation study above. In this instance, the control oil was extra virgin olive oil rather than canola oil. A salad dressing made from the olive oil was subjected to sensory evaluation in comparison with a salad dressing made from the healthy oil. 82% of the panelists indicated that they preferred the healthy oil salad dressing to the extra virgin olive oil salad dressing. This is a statistically significant difference at a very high level of confidence.

Chicken Frying Evaluation

Chicken pieces were fried in either extra virgin olive oil or in the healthy oil of this Example. 39 participants tasted the fried chicken and rated same on a scale of 1 through 5, with 1 indicating extreme liking and 5 indicating extreme disliking. The panel of participants rated the fried chicken in eight categories. In six of the categories, there was no statistical difference between chicken cooked in the two oils. In two of the categories, flavor acceptability and aftertaste, the chicken fried in the healthy oil was statistically better in terms of positive preference than was the chicken cooked in the extra virgin olive oil. In each of the eight sensory categories, a t-Test was performed, each being a two-sample assuming equal variances. The data are presented in Table III, which reports values with rounding at four significant figures.

TABLE III

| | "Healthy" Oil | Olive Oil |
|---|---|---|
| Overall Appearance Acceptability | | |
| Mean | 2.344 | 2.423 |
| Variance | 1.067 | 0.823 |
| Observations | 39 | 39 |
| Pooled Variance | 0.945 | |
| Hypothesized Mean Difference | 0 | |
| Df | 76 | |
| t Stat | −0.361 | |
| P(T <= t) one-tail | 0.360 | |
| t Critical one-tail | 1.665 | |
| P(T <= t) two-tail | 0.719 | |
| t Critical two-tail | 1.992 | |
| Acceptability of Color | | |
| Mean | 2.208 | 2.397 |
| Variance | 0.851 | 0.660 |
| Observations | 39 | 39 |
| Pooled Variance | 0.755 | |
| Hypothesized Mean Difference | 0 | |
| Df | 76 | |
| t Stat | −0.964 | |
| P(T <= t) one-tail | 0.169 | |
| t Critical one-tail | 1.665 | |
| P(T <= t) two-tail | 0.338 | |
| t Critical two-tail | 1.992 | |

TABLE III-continued

|  | "Healthy" Oil | Olive Oil |
|---|---|---|
| Flavor Acceptability | | |
| Mean | 2.357 | 2.808 |
| Variance | 0.676 | 1.153 |
| Observations | 37 | 39 |
| Pooled Variance | 0.921 | |
| Hypothesized Mean Difference | 0 | |
| Df | 74 | |
| t Stat | −2.048 | |
| P(T <= t) one-tail | 0.022 | |
| t Critical one-tail | 1.666 | |
| P(T <= t) two-tail | 0.044 | |
| t Critical two-tail | 1.993 | |
| Mouthfeel/Texture Acceptability | | |
| Mean | 2.8 | 2.997 |
| Variance | 1.223 | 1.369 |
| Observations | 39 | 39 |
| Pooled Variance | 1.296 | |
| Hypothesized Mean Difference | 0 | |
| Df | 76 | |
| t Stat | −0.766 | |
| P(T <= t) one-tail | 0.223 | |
| t Critical one-tail | 1.665 | |
| P(T <= t) two-tail | 0.446 | |
| t Critical two-tail | 1.992 | |
| Eating Quality | | |
| Mean | 2.770 | 3.113 |
| Variance | 1.064 | 1.265 |
| Observations | 37 | 38 |
| Pooled Variance | 1.1658 | |
| Hypothesized Mean Difference | 0 | |
| Df | 73 | |
| t Stat | −1.375 | |
| P(T <= t) one-tail | 0.087 | |
| t Critical one-tail | 1.666 | |
| P(T <= t) two-tail | 0.173 | |
| Acidity/Bitterness | | |
| Mean | 2.605 | 2.974 |
| Variance | 0.570 | 0.868 |
| Observations | 38 | 39 |
| Pooled Variance | 0.721 | |
| Hypothesized Mean Difference | 0 | |
| Df | 75 | |
| t Stat | −1.907 | |
| P(T <= t) one-tail | 0.030 | |
| t Critical one-tail | 1.665 | |
| P(T <= t) two-tail | 0.060 | |
| t Critical two-tail | 1.992 | |
| Aftertaste | | |
| Mean | 2.378 | 2.974 |
| Variance | 0.575 | 1.184 |
| Observations | 37 | 39 |
| Pooled Variance | 0.888 | |
| Hypothesized Mean Difference | 0 | |
| Df | 74 | |
| t Stat | −2.757 | |
| P(T <= t) one-tail | 0.004 | |
| t Critical one-tail | 1.666 | |
| P(T <= t) two-tail | 0.007 | |
| t Critical two-tail | 1.992 | |
| Overall Acceptability | | |
| Mean | 2.603 | 2.936 |
| Variance | 0.923 | 1.318 |
| Observations | 39 | 39 |
| Pooled Variance | 1.121 | |
| Hypothesized Mean Difference | 0 | |
| Df | 76 | |
| t Stat | −1.390 | |
| P(T <= t) one-tail | 0.084 | |
| t Critical one-tail | 1.665 | |
| P(T <= t) two-tail | 0.168 | |
| t Critical two-tail | 1.991 | |

EXAMPLE 2

A structured lipid was made substantially in accordance with Example 1. The charge was 50% identity preserved canola oil and 50% NEOBEE® 1053 MCT oil. Interesterification and deodorization proceeded. The structured lipid had a smoke point of 207° C. (405° F.). Further analysis showed an SFC at 10° C. of 0.55, an Iodine Value of 49.5 and an OSI of 10.65 hours at 110° C. Its peroxide value was less than 0.1, and the free fatty acids were at 0.02. C8 analysis was 18.54%, and C10 analysis was 17.41%, with percent "trans" being 0.84%. Analyzed total saturates was 41.93%. This structured lipid is formulated into a "healthy" oil as described herein by blending same with a phytosterol ester, the structured lipid being at 92 weight percent and the phytosterol being at 8 weight percent, based on the total weight of the healthy oil.

EXAMPLE 3

Chemical interesterification was carried out substantially in accordance with Example 1. The charges were 65 percent by weight of BUNGE® non-hydrogenated corn oil and 35 percent by weight of C8/C10 medium chain triglyceride. The resulting structured lipid was treated to remove soaps and subjected to deodorization. The color measurement was 8.0 Y/1.0 R. Analysis showed that the Brookfield viscosity was 48 centipoise at 20° C. with a spindle No. 4 at 50 rpm. The smoke point was 214.5° C. (418° F.). This structured lipid is formulated into a "healthy" oil as described herein by blending same with a phytosterol ester, the structured lipid being at 93 weight percent and the phytosterol being at 7 weight percent, based on the total weight of the healthy oil.

EXAMPLE 4

Soybean oil and MCTs were charged to a reaction vessel at a ratio of 65:35 of soy:MCT. The resulting interesterified structured lipid had a viscosity of 44 centipoise at 20° C. on the Brookfield viscometer with spindle No. 4 at 50 rpm. The smoke point was 213.3° C. (416° F.). The color measurement was 13.0 Y/2.0 R. When made up into a physical blend product in the same proportions, the same oil and MCT had a Brookfield viscosity at 20° C., with spindle No. 4 at 50 rpm, of 56 cps, and the smoke point was 179° C. (354° F.). The soybean oil, prior to blending, had a viscosity of 60 cp measured in the same manner. This structured lipid is formulated into a "healthy" oil as described herein by blending same with a phytosterol ester, the structured lipid being at 94 weight percent and the phytosterol ester being at 6 weight percent, based on the total weight of the healthy oil.

EXAMPLE 5

Interesterification was carried out on a charge of 32.5 weight percent corn oil, 32.5 weight percent cottonseed oil, and 35 weight percent MCTs. The corn oil had a Brookfield viscosity of 64 cps measured as in Example 1. After proceeding substantially in accordance with Example 1, the thus prepared structured lipid had a Brookfield viscosity at 20° C., with spindle No. 4 at 50 rpm, of 48 centipoise. The smoke point was 201° C. (394° F.). The color measurement was 22.0 Y/2.9 R. When made into a physical blend product in the same proportions, these same components gave a Brookfield viscosity of 56 cp and a smoke point of 176.7° C. (350° F.), measured in the same manner. This structured lipid is formulated into a "healthy" oil as described herein by blending same with a phytosterol ester, the structured lipid being at 93 weight percent and the phytosterol ester being at 7 weight percent, based on the total weight of the healthy oil.

EXAMPLE 6

BUNGE® corn oil (65 weight percent) and 35 weight percent MCTs having 70% C10 were subjected to a randomizing interesterification reaction substantially in accordance with Example 1. The resulting structured lipid had a Brookfield viscosity of 48 cps, with the No. 4 spindle at 50 rpm, at 20° C. The smoke point was 199° C. (390° F.). The color measurement was 9.0 Y/1.5 R. This structured lipid is formulated into a "healthy" oil as described herein by blending same with a phytosterol ester, the structured lipid being at 92 weight percent and the phytosterol ester being at 8 weight percent, based on the total weight of the healthy oil.

EXAMPLE 7

A charge into the interesterification process substantially in accordance with Example 1 was as follows: soybean oil at 40 weight percent, cottonseed oil at 25 weight percent, and MCTs at 35 weight percent. The resulting structured lipid had a Brookfield viscosity of 48 centipoise with spindle No. 4 at 50 rpm and at 20° C. The smoke point was 198° C. (388° F.). The color measurement was 22.0 Y/3.3 R. A physical blend product made of these same components in the same proportions had a Brookfield viscosity under the same conditions of 56 cp and a smoke point of 172° C. (342° F.). This structured lipid is formulated into a "healthy" oil as described herein by blending same with a phytosterol ester, the structured lipid being at 94 weight percent and the phytosterol ester being at 6 weight percent, based on the total weight of the healthy oil.

EXAMPLE 8

A charge into the interesterification process substantially in accordance with Example 1 was as follows: soybean oil at 60 weight percent, cottonseed oil at 25 weight percent, and MCTs at 15 weight percent. The resulting structured lipid had a Brookfield viscosity of 40 centipoise with spindle No. 4 at 50 rpm and at 20° C. The smoke point was 203.3° C. (398° F.). The color measurement was 22. Y/3.5 R. A physical blend of these same components in these proportions had a Brookfield viscosity of 48 cps and a smoke point of 183° C. (362° F.), measured in accordance with this Example. This structured lipid is formulated into a "healthy" oil as described herein by blending same with a phytosterol ester, the structured lipid being at 95 weight percent and the phytosterol being at 5 weight percent, based on the total weight of the healthy oil.

EXAMPLE 9

Soybean oil and MCTs were charged to a reaction vessel at a ratio of 75:25 of soy:MCT. The resulting interesterified structured lipid had a viscosity of 44 centipoise at 20° C. on the Brookfield viscometer with spindle No. 4 at 50 rpm. The color measurement was 4.5 Y/1.9 R. The smoke point was 210° C. (410° F.). A physical blend of these components in these same proportions gave a Brookfield viscosity of 56 cps and a smoke point of 175.5° C. (348° F.), measured in accordance with this Example. This structured lipid is formulated into a "healthy" oil as described herein by blending same with a phytosterol ester, the structured lipid being at 92 weight percent and the phytosterol being at 8 weight percent, based on the total weight of the healthy oil.

EXAMPLE 10

Canola oil (Natreon identity preserved oil) and MCTs were charged to a reaction vessel at a ratio of 60:40 of oil:MCT. The resulting interesterified structured lipid had a viscosity of 44 centipoise at 20° C. on the Brookfield viscometer with spindle No. 4 at 50 rpm. The smoke point was 197.8° C. (388° F.). A physical blend product of these components at these proportions had a Brookfield viscosity of 48 cps and a smoke pint of 187.8° (370° F.), measured according to this Example. This structured lipid is formulated into a "healthy" oil as described herein by blending same with a phytosterol ester, the structured lipid being at 92 weight percent and the phytosterol components being at 8 weight percent, based on the total weight of the healthy oil.

EXAMPLE 11

Interesterification was carried out on a charge of 70 weight percent canola oil (Natreon oil) and 30 weight percent MCTs. After proceeding substantially in accordance with Example 1, the thus prepared structured lipid had a Brookfield viscosity at 20° C., with spindle No. 4 at 50 rpm, of 48 centipoise. The smoke point was 202° C. (396° F.). A same-proportion physical blend product of these had a Brookfield viscosity of 52 cps and a smoke point of 182.2° C. (360° F.) measured according to this Example. This structured lipid is formulated into a "healthy" oil as described herein by blending same with a phytosterol ester, the structured lipid being at 92 weight percent and the phytosterol being at 8 weight percent, based on the total weight of the healthy oil.

EXAMPLE 12

BUNGE® corn oil (70 weight percent) and 30 weight percent MCTs were subjected to a randomizing interesterification reaction substantially in accordance with Example 1. The resulting structured lipid had a Brookfield viscosity of 48 cps, with the No. 4 spindle at 50 rpm, at 20° C. The smoke point was 214.4° C. (418° F.). A same-proportion physical blend of these had a Brookfield viscosity of 48 cps and a smoke point of 180° C. (356° F.) measured according to this Example. This structured lipid is formulated into a "healthy" oil as described herein by blending same with a phytosterol ester, the structured lipid being at 92 weight percent and the phytosterol ester being at 8 weight percent, based on the total weight of the healthy oil.

EXAMPLE 13

A charge into the interesterification process substantially in accordance with Example 1 was as follows: canola oil at 60 weight percent and MCTs at 40 weight percent. The resulting structured lipid had a Brookfield viscosity of 40 centipoise with spindle No. 4 at 50 rpm and at 20° C. The smoke point was 194.4° C. (382° F.). A physical blend of these components in the same proportion, when tested according to this Example, gave a Brookfield viscosity of 44 cps and a smoke point of 175.5° C. (348° F.). Canola oil, before blending or reaction, had a viscosity of 64 cps, measured in the same manner. This structured lipid is formulated into a "healthy" oil as described herein by blending same with a phytosterol ester, the structured lipid being at 92 weight percent and the phytosterol ester being at 8 weight percent, based on the total weight of the healthy oil.

EXAMPLE 14

A charge into the interesterification process substantially in accordance with Example 1 was as follows: canola oil at 70 weight percent and MCTs at 30 weight percent. The resulting structured lipid had a Brookfield viscosity of 40 centipoise with spindle No. 4 at 50 rpm and at 20° C. The smoke point was 212.2° C. (414° F.). A physical blend of these reactants in the same proportion, when tested according to this Example, gave a Brookfield viscosity of 48 cps and a smoke point of 180° C. (356° F.). This structured lipid is formulated into a "healthy" oil as described herein by blending same with a phytosterol ester, the structured lipid being at 93 weight percent and the phytosterol being at 7 weight percent, based on the total weight of the healthy oil.

EXAMPLE 15

The structured lipid-based phytosterol-containing composition of Example 1 was evaluated in multiple food applications. The following illustrates the levels at which cholesterol adsorption can be reduced with this composition when compared with a commercial edible oil. St-Onge et al., "Phytosterols and Human Lipid Metabolism: Efficacy, Safety and Novel Foods," *Lipids*, Volume 38, No. 4 (2003) indicates that intakes of 150 and 300 mg of phytosterols added to sterol-free edible oil can reduce total cholesterol adsorption by 12.1% and 27.9%, respectively. Recommended daily allowances of vegetables according to 21 C.F.R. 101.12 is 110 grams of vegetables. When a phytosterol ester component was added to refined, bleached and deodorized canola oil (control oil) and used to stirfry vegetables, 90 mg of phytosterol component were found to be within the 110 grams of vegetables. When the structured lipid phytosterol ester composition of this Example was substituted for the canola oil, 410 mg of phytosterol component were found to be within the 110 grams of vegetables. This represents a phytosterol delivery enhancement of over 4.5 times.

For chicken, the recommended amount according to the 21 C.F.R. 101.12 reference is 55 grams of chicken. When 55 grams of chicken were pan fried with the canola oil control, 30 mg of phytosterol component were found in the chicken, whereas when the structured lipid phytosterol ester oil was used, 200 mg of phytosterol component were on or in the chicken. The chicken that was pan fried in the structured lipid oil contained over 6.6 times of the phytosterol delivered when the control oil was used.

Muffins also have a 21 C.F.R. 101.12 daily value reference amount of 55 grams. When blueberry muffins were baked with the control canola oil as the oil component of the batter, 30 mg of phytosterol component were found within the baked muffin. When the structured lipid phytosterol ester oil was used, 160 mg of phytosterol component were included within the 55 grams of muffin. The structured lipid oil composition resulted in delivery of over 5.3 percent more sterol than the control oil when the control oil was used in the muffin batter.

The 21 C.F.R. 101.12 reference amount for cake is 80 grams. When cake was baked from a yellow cake batter including the control canola oil, the amount of sterol ester was 50 mg per 80 grams of yellow cake. When the structured lipid phytosterol ester oil was used in the yellow cake batter, 300 mg of sterol esters were delivered per 80 grams of yellow cake. This represents a 6-fold increase in sterol ester delivery when using the structured lipid.

A waffle has a daily value reference amount according to 21 C.F.R. 101.12 of 85 grams. When the control canola oil was used in a waffle batter baked into waffles, the amount of sterol esters found within the waffles was 10 mg per 85 grams of waffle. When the structured lipid phytosterol ester was used instead of the control oil, 70 mg of sterol esters were delivered into the baked waffle per 85 grams of waffle. This represented a 7-fold increase in sterol delivery by utilizing the structured lipid sterol composition of this Example.

EXAMPLE 16

Clinical testing was conducted for evaluating the effects of certain edible oils on circulating lipid or cholesterol levels, weight control, body composition and energy expenditure in overweight, hypercholesterolemic men. One of the oils was a structured lipid phytosterol oil composition of 93.8 weight percent of the structured lipid prepared in accordance with Example 1, 6.0 weight percent sterol esters, and 0.2 weight percent polyglycerol ester (PGE). This was prepared by adding the sterol esters and PGE in a liquid state into the structured lipid into a mixing vessel until the sterol ester and PGE were completely dissolved. Mixing continued, with heat as needed, to prepare a transparent liquid that is the structured lipid phytosterol composition of this Example 16. The other edible oil was extra virgin olive oil.

The individual subjects for the study fell within the categories of healthy overweight (body mass index between 25-33 kg/m$^2$), light to moderately active hypercholesterolemic and between 18 and 45 years of age. Each subject was a male non-smoker who was not a regular consumer of alcohol. Subjects were excluded if they had a medical history of cardiovascular disease, gastrointestinal, hepatic, renal, or endocrine disorders or if he was taking any lipid-lowering or anti-hypertensive medication. Only individuals on stable doses of other medications were included in the study. Also, subjects with a particular taste aversion or allergy to any of the common foods included in the menus were not selected.

Diet Protocol

The study was a randomized single-blind, crossover trial consisting of two independent phases of six weeks each and an intermediary washout period of 4 to 8 weeks. Experimental diets consisted of prepared North American solid foods, precisely weighed, and based on a 3-day rotating cycle menu. Diets were served as three isoenergetic meals per day and provided 45% of energy as carbohydrate, 15% as protein, and 40% as fat, of which 75% was delivered as treatment fat. The remaining 25% of total fat was found in the basal diet food items identical to both diets. Treatment fat, either the structured lipid phytosterol composition (hereinafter "test lipid") or extra virgin olive oil, was directly incorporated into the food items during meal preparation and cooking to effect blinding. The test lipid contained approximately 1.3 g/1000 kcal of unesterified phytosterols. Differences in the fatty acid content of the two oils were accounted for in setting meal energy content. The different energetic contribution of the medium chain triglyceride and of the long chain triglyceride, 34 and 38 kJ/g, respectively, were accounted for in the calculation of energy intake; hence the test lipid and the extra virgin olive diets were isoenergetic. The intake of each fat component was equally distributed over the three meals. Contents of non-fat and non-sterol constituents were identical across diets.

To provide the targeted energy balanced diet, the nutrient intake was adjusted to individual subject energy requirements using the Mifflin equation, to which an activity factor of 1.7 was multiplied to compensate for energy needs of active adults. During the first week of phase 1, energy intake was readjusted to re-establish energy balance. Energy intake was fixed and was identical during both dietary treatment phases. Body weight was monitored daily before breakfast or the supper feeding period. No extra food was allowed between meals, except for decaffeinated, energy-free carbonated beverages and herbal teas, which were obtained from the kitchen staff. One black coffee was allowed per day at breakfast. The Dietary Recommended Intakes (DRI's) were met for all vitamins, minerals, fiber, carbohydrate subcomponents, and essential fatty acids. The nutrient content of the diets were determined with Food Processor (ESHA Research, Salem, Oreg.), a computerized dietary analysis program. A weight maintenance protocol was chosen to specifically determine the effects of the treatment oil, not weight loss, on the different parameters measured. The composition of the diet (relative composition by calories) included 30% of either extra virgin olive oil or the test lipid, plus 45% carbohydrate, 40% fat, 2% saturated, 7% monounsaturated, 1% polyunsaturated, and 15% protein.

The subjects were instructed to return any uneaten food waste to the clinic in order to routinely assess compliance to dietary protocol. Although the energy expenditure resulting from physical activity was not measured directly, subjects were required to maintain a constant physical activity level during each of the two experimental phases.

Tests and Analyses

Fasting blood samples of 2×10 ml plasma EDTA and 1×5 ml serum Vacutainer tubes were collected on days 1, 2, 41 and 42 of each experimental phase. Blood samples were then centrifuged at 1500 rpm for 20-25 minutes, and plasma, serum and red blood cells were, immediately separated into aliquots and stored at −80° C. for subsequent analysis. TC, LDL, HDL and TG levels were thereafter quantified in duplicate in the laboratory.

Plasma lipid aliquots were analyzed for total cholesterol (TC), HDL cholesterol (HDL), and triglycerides (TG), which were measured using standard reagents and a VP Autoanalyzer (Abbott Laboratories, North Chicago, Ill.). An enzymatic colorimetric test (Enzymatic kit—Roche Diagnostics) with cholesterol esterase and cholesterol oxidase as enzymes were used for TC and TG. HDL determination was performed by prior precipitation of the apo-B subfraction of plasma with dextrin sulphate and magnesium chloride and subsequent ultracentrifugation. The LDL cholesterol (LDL) subfraction was indirectly quantified using the Friedewald equation (Friedewald 1972) as indicated by the following: LDL=TC−(HDL+TG/5).

Subjects underwent MRI scans once during both week 1 and week 6 of each experimental phase, with a total of 4 data sets. The MRI unit was a Siemens 1.5 Tesla Magnetom VISION scanner. Each subject was in a ventral prone position in the magnet with his arms stretched above his head in order to limit the artifacts created by respiratory motion of the thoracic cage. Subjects had whole body scans from fingers to toes. The scans comprised two parts: the upper and lower body, and lasted 30-45 minutes, on average. A series of 40-47 T1-weighted axial spin echo images, 10 mm in width, were taken every 350 mm. The landmark for scout images were centered at the lumbar vertebrae L4-L5 and the femoral and humeral heads, in order to distinguish upper, abdominal and lower sections of the body. Changes in body compartment volumes of total, subcutaneous, visceral and intra-muscular adipose tissue, as well as lean body, muscle and bone mass were measured. The MRI data were integrated using the Slice-O-Matic software (TomoVision). Total and regional distribution of subcutaneous, visceral and intra-myocellular adipose tissue as well as abdominal fat were quantified by calculating the total pixel area and subsequent volume for a specific tissue, following differences in grey intensity of the picture. Regional quantification for abdominal fat was achieved by integrating all MRI axial slices taken between the femoral heads and the top of the liver/base of the lungs. A coefficient of 0.92 $g/cm^3$ was used to convert adipose tissue volumes to mass values.

Energy expenditure (EE) was measured with a metabolic monitor (Deltatrac, Sensor Medics, Anaheim, Calif.) during the first week and the sixth week for the subjects. The metabolic monitor was calibrated daily using gas containing 95% $O_2$ and 5% $CO_2$ at ambient pressure. Expired gases were analyzed against ambient air. Subjects were required to undergo a 12 hour overnight fasting period prior to each measurement period. EE was then measured at the CNRU 30 minutes prior to the consumption of a standard breakfast. After this initial resting period, the RMR was assessed using indirect calorimetry with ventilated hood methodology. Subjects were required to consume the breakfast within a 30-minute period, after which EE measurements resumed for 5.5 hours. EE was measured continuously after breakfast.

Statistical analysis of the data generally utilized the mean±standard error of the mean. Data for blood lipid levels and EE/substrate oxidation for each phase (extra virgin olive oil and test lipid) were analyzed using a paired t-test to determine significant changes from baseline. The blood lipid levels and EE/substrate oxidation data also were analyzed using a paired t-test to identify any significant changes between the two diets (extra virgin olive oil and test lipid) from baseline to endpoint. Absolute differences between baseline and endpoint data from respective subjects' blood lipids and EE/substrate oxidation data were calculated to determine if there was a significant change using paired t-test procedures. Body composition analysis data were expressed as the least square means±standard error of the mean for the different adipose tissue compartment volumes/areas for both the extra virgin olive oil and test lipid diets. A student t-test was also calculated to state the significance of the difference between diets. Change and percent change of total (TAT), subcutaneous (SAT), abdominal (AbAT), intra-myocellular (IMAT) and visceral (VAT) across diets at the start of the study were compared using a one-way analysis of variance. The data were merged for analysis using SAS statistical software (SAS Institute, Cary N.C.). A value $p<0.05$ was used to determine significance.

A total of 23 subjects completed the study. Table IV summarizes the characteristics of these subjects.

TABLE IV

| | Average of Group (n = 23) | ±SEM | Normal Values For Healthy Individuals |
|---|---|---|---|
| Age (years) | 37 | 1.33 | N/A |
| Weight (kg) | 87.13 | 2.23 | N/A |
| BMI ($kg/m^2$) | 28.55 | 0.59 | 20-25 |
| TC (mmol/L) | 5.90 | 0.2 | <4.14 |
| LDL-C (mMol/L) | 3.92 | 0.19 | <2.5 |
| HDL-C (mMol/L) | 1.19 | 0.7 | >1.0 |
| TG (mMol/L) | 1.92 | 0.14 | <1.7 |
| CVD Factor | 5.26 | 0.29 | <5.00 |
| Calculated Energy Req'ts (Kcal) | 3056 | 66 | N/A |

The respective weights of the subjects at baseline were similar for the extra virgin olive oil and for the test lipid (96.34 and 86.33 Kg, respectively). Both the extra virgin olive oil and test lipid group lost a significant amount of weight (−1.22 kg and −1.68 kg, respectively) after the 6 week study period. Subjects on the test lipid diet lost more weight (0.45 kg) than on the extra virgin olive oil diet; however, the difference between groups did not attain statistical significance.

Cholesterol and Triglyceride Levels

The TC values decreased significantly (p<0.0001) from baseline to endpoint in the test lipid phase, 5.68±0.21 to 4.71±0.16 mMol/L. See Table V. A similar trend was seen with extra virgin olive oil but to a lesser extent (p=0.0001), from 5.73±0.18 at baseline to 5.14±0.19 mMol/L at endpoint. The endpoint TC after test lipid consumption was statistically lower than that of extra virgin olive oil (p=0.0006), while the baseline TC data was not statistically different between treatments (p=0.7075).

The LDL decreased significantly with the test lipid consumption from baseline (3.95±0.19) to endpoint (3.12±0.16 mMol/L (p<0.0001)). See Table V. The extra virgin olive oil also showed a significant decrease in LDL from 4.00±0.18 to 3.54±0.18 mMol/L (p=0.0002). The endpoints were statistically different (p=0.0002). The test lipid expressed a significantly greater decrease in LDL compared to extra virgin olive oil, even though the baseline values for olive oil and test lipid were similar (p=0.69).

The HDL decreased non-significantly in both the test lipid and the extra virgin olive oil, from 0.91±0.04 to 0.89±0.03 mMol/L and 0.97±0.07 to 0.93±0.04 mMol/L, respectively. See Table V. The values for HDL did not exhibit statistically significant differences between the baseline and endpoint data for test lipid compared to extra virgin olive oil.

The TG decreased significantly in the test lipid from 1.81±0.14 to 1.53±0.11 mMol/L (p=0.01). A statistically similar decrease was seen in extra virgin olive oil from 1.69±0.15 to 1.48±0.13 mMol/L (p=0.02). See Table V. There were no statistically significant differences between the baseline and endpoint data for TG values for test lipid versus the extra virgin olive oil. Table V reports changes in blood lipids in hypercholesterolemic men after six weeks.

Table VI reports these changes in terms of percentage reduction for each of total cholesterol, LDL cholesterol, HDL cholesterol and triglycerides. This table reports the overall percentage change in blood lipid concentrations in hypercholesterolemic men after six weeks.

TABLE VI

|     | Extra Virgin Olive oil (% Change) | Test Lipid (% Change) |
| --- | --- | --- |
| TC  | −10.39% | −17.01% |
| LDL | −11.45% | −21.01% |
| HDL | −4.23%  | −1.44%  |
| TG  | −12.85% | −15.12% |

Adipose Tissue Differences

Twenty-three patients underwent magnetic resonance imaging at baseline and endpoint of each experimental phase. Twenty (n=20) sets were used for analysis, because of technical issues. The characteristics of the patients are summarized in Table IV. Tables VII, VIII and IX report the changes observed for both the control (extra virgin olive oil) and test lipid diet groups in total (TAT), subcutaneous (SAT), abdominal (AbAT), intra-myocellular (IMAT) and visceral (VAT) adipose tissue. The data are expressed as volumes ($cm^3$—Table VII) and extrapolated to masses (kg—Table VIII). Data are also presented as surface areas ($cm^2$—Table IX).

Over the period of the study, total adipose tissue mass (TAT), which refers to the sum of all sub-compartments of adipose tissue that were analyzed (SAT, AbAT, IMAT, VAT, pelvic, thoracic and head adipose tissue surrounding the head), decreased slightly in the test lipid group (−0.22±0.09 kg, p<0.05) and in the extra virgin olive oil control group (−0.17±0.09 kg, p=0.0739). This means that for each diet, the change in TAT was significantly different from baseline.

TABLE V

| | Extra Virgin Olive oil (n = 23) | | | | | Test Lipid (n = 23) | | | | | Between Group P | |
| --- | --- | --- | --- | --- | --- | --- | --- | --- | --- | --- | --- | --- |
| | Base | ±SEM | End | ±SEM | P | Base | ±SEM | End | ±SEM | P | Base P | End P |
| TC | | | | | | | | | | | | |
| Day 1 | 5.66 | 0.18 | 5.13 | 0.2 | .0008* | 5.67 | 0.22 | 4.67 | 0.16 | <.0001* | NS | .0019* |
| Day 2 | 5.81 | 0.19 | 5.14 | 0.17 | <.0001* | 5.68 | 0.22 | 4.75 | 0.16 | <.0001* | NS | .0005* |
| Average | 5.73 | 0.18 | 5.14 | 0.19 | .0001* | 5.68 | 0.21 | 4.71 | 0.16 | <.0001* | NS | .0006* |
| Difference | | | 0.60 | 0.13 | | | | 0.97 | 0.17 | | | .0592 |
| LDL | | | | | | | | | | | | |
| Day 1 | 3.91 | 0.18 | 3.54 | 0.20 | .0044* | 3.90 | 0.2 | 3.10 | 0.16 | <.0001* | NS | .0004* |
| Day 2 | 4.08 | 0.19 | 3.54 | 0.17 | <.0001* | 4.00 | 0.2 | 3.14 | 0.16 | <.0001* | NS | .0004* |
| Average | 4.00 | 0.18 | 3.54 | 0.18 | .0002* | 3.95 | 0.19 | 3.12 | 0.16 | <.0001* | NS | .0003* |
| Difference | | | 0.46 | 0.1 | | | | 0.83 | 0.15 | | | .0221* |
| HDL | | | | | | | | | | | | |
| Day 1 | 0.95 | 0.06 | 0.91 | 0.04 | NS | 0.89 | 0.04 | 0.89 | 0.03 | NS | NS | NS |
| Day 2 | 0.99 | 0.07 | 0.94 | 0.05 | NS | 0.92 | 0.04 | 0.90 | 0.04 | NS | NS | NS |
| Average | 0.97 | 0.07 | 0.93 | 0.04 | NS | 0.91 | 0.04 | 0.89 | 0.03 | NS | NS | NS |
| Difference | | | 0.04 | 0.04 | | | | 0.02 | | | | NS |
| TG | | | | | | | | | | | | |
| Day 1 | 1.76 | 0.18 | 1.49 | 0.13 | .0281* | 1.93 | 0.2 | 1.50 | 0.12 | .0091* | NS | NS |
| Day 2 | 1.63 | 0.13 | 1.47 | 0.13 | NS | 1.68 | 0.1 | 1.57 | 0.12 | NS | NS | NS |
| Average | 1.69 | 0.15 | 1.48 | 0.13 | .0195* | 1.81 | 0.14 | 1.53 | 0.11 | .0105* | NS | NS |
| Difference | | | 0.22 | 0.09 | | | | 0.27 | 0.1 | | | NS |

*Significant differences observed.
Base = Baseline Mean Values,
±SEM = Standard Error to Mean,
End = Endpoint Mean Values,
Base P = Baseline Probability Values Between Group,
End P = Endpoint Probability Value Between Group.

These differences were significant in TAT across time. They were not significant across diets (p=0.6814).

Subcutaneous adipose tissue (SAT), which refers to the fat which is contained in the periphery, under the skin, was reduced in both the control group (−0.15±0.07 kg, p<0.05) and in the test lipid group (−0.19±0.04 kg, p<0.01) across time although the effect on SAT between diets did not achieve a level of statistical significance (p=0.5834). Abdominal adipose tissue (AbAT) represents the pelvic adipose tissue (around the L4-L5 vertebrae), visceral (around the abdomen/intestines, between L4-L5 vertebrae and the base of the lungs) and thoracic (the lungs) compartments of adipose tissue. None of the results for this parameter were statistically significant across time (control group: −0.04±0.03 kg; p=0.1856 and Delta group: −0.01±0.03 kg; p=0.8085) or between diets (p=0.3225). Intra-myocellular (or muscular) adipose tissue, refers to the fat contained within or surrounding muscle fibers. No statistically significant change in either the control or the test lipid group (−0.01±0.01 kg; NS) over the study period as a change from baseline or between diets (p=0.7827) was found. Visceral adiposity showed a statistically significant change from baseline in the control group (−0.05±0.03 kg; p<0.05), not in the test lipid group (−0.02±0.03 kg; p=0.4841), and there was no significant difference between diets (p=0.3289).

Table VII reports upon changes in body adipose tissue sub-compartment volumes in overweight (n=20) men after six weeks.

TABLE VII

|  | Extra Virgin Olive oil | ±SEM | P valve | Test Lipid | ±SEM | P value | Estimate of difference between diets | ±SEM | Between diets p value |
|---|---|---|---|---|---|---|---|---|---|
| TAT[1] |  |  |  |  |  |  |  |  |  |
| Change (cm3) | −1230.65 | 866.75 | 0.1643 | −1730.19 | 866.75 | 0.0535 | 499.55 | 1177.66 | 0.674 |
| % Change | −2.3726 | 2.0516 | 0.2552 | −4.379 | 2.0516 | 0.0398* | 2.0064 | 2.7435 | 0.474 |
| SAT |  |  |  |  |  |  |  |  |  |
| Change (cm3) | −906.63 | 680.23 | 0.191 | −1687.26 | 680.23 | 0.0179* | 780.63 | 902.46 | 0.3928 |
| % Change | −2.5168 | 2.1935 | 0.2588 | −5.4389 | 2.1935 | 0.018* | 2.9222 | 3.0066 | 0.344 |
| AbAT[2] |  |  |  |  |  |  |  |  |  |
| Change (cm3) | −165.54 | 262.34 | 0.532 | 6.6087 | 262.34 | 0.98 | −172.15 | 371 | 0.6454 |
| % Change | 1.8713 | 4.4233 | 0.6748 | 0.3261 | 4.4233 | 0.9416 | 1.5452 | 6.2555 | 0.8063 |
| IMAT |  |  |  |  |  |  |  |  |  |
| Change (cm3) | −157.57 | 85.4077 | 0.0734 | −121.73 | 85.4077 | 0.1628 | −35.8395 | 113.11 | 0.755 |
| % Change | −7.0042 | 4.4074 | 0.1209 | −5.8591 | 4.4074 | 0.1922 | −1.1451 | 5.8528 | 0.8471 |
| VAT |  |  |  |  |  |  |  |  |  |
| Change (cm3) | −925.33 | 343.43 | 0.0107* | −21.0398 | 343.43 | 0.9515 | −904.29 | 461.87 | 0.0659 |
| % Change | −5.8596 | 6.6839 | 0.3865 | 1.6103 | 6.6839 | 0.811 | −7.4699 | 9.4525 | 0.4346 |

Significance value (*p < 0.05). Data is expressed as mean ± SEM (standard error of the mean).
[1]Sum of all fat compartment volumes.
[2]Sum of pelvic, visceral and thoracic fat volumes. Between group difference = statistical significance between diets.

Table VIII reports changes in body adipose tissue sub-compartment mass in overweight (n=20) men after six weeks.

TABLE VIII

|  | Extra Virgin Olive oil | ±SEM | p value | Test Lipid | ±SEM | P value | Estimate of difference between diets | ±SEM | p value Between diets |
|---|---|---|---|---|---|---|---|---|---|
| TAT[1] |  |  |  |  |  |  |  |  |  |
| Change (kg) | −0.17 | 0.09 | 0.0739 | −0.22 | 0.09 | 0.027* | 0.04 | 0.11 | 0.6814 |
| % Change | 0.00 | 0.00 | 0.1733 | 0.00 | 0.00 | 0.0461* | 0.00 | 0.00 | 0.5759 |
| SAT |  |  |  |  |  |  |  |  |  |
| Change (kg) | −0.15 | 0.07 | 0.0379* | −0.19 | 0.04 | 0.0086** | 0.04 | 0.08 | 0.5834 |
| % Change | 0.00 | 0.00 | 0.0544 | 0.00 | 0.00 | 0.0039** | 0.00 | 0.00 | 0.373 |
| AbAT[2] |  |  |  |  |  |  |  |  |  |
| Change (kg) | −0.04 | 0.03 | 0.1856 | −0.01 | 0.03 | 0.8085 | −0.03 | 0.03 | 0.3255 |
| % Change | 0.00 | 0.00 | 0.1968 | 0.00 | 0.00 | 0.7359 | 0.00 | 0.00 | 0.4679 |
| IMAT |  |  |  |  |  |  |  |  |  |
| Change (kg) | −0.01 | 0.01 | 0.5969 | −0.01 | 0.01 | 0.3603 | 0.01 | 0.02 |  |
| % Change | 0.00 | 0.00 | 0.6478 | 0.00 | 0.00 | 0.322 | 0.00 | 0.00 | 0.7827 |
|  |  |  |  |  |  |  |  |  | 0.7031 |
| VAT |  |  |  |  |  |  |  |  |  |
| Change (kg) | −0.05 | 0.03 | 0.0423* | −0.02 | 0.03 | 0.4841 | −0.04 | 0.03 | 0.3289 |
| % Change | −0.01 | 0.01 | 0.1052 | 0.00 | 0.01 | 0.7075 | −0.01 | 0.01 | 0.3747 |

TABLE VIII-continued

|  | Extra Virgin Olive oil | ±SEM | p value | Test Lipid | ±SEM | P value | Estimate of difference between diets | ±SEM | p value Between diets |
|---|---|---|---|---|---|---|---|---|---|
| TOT[3] | | | | | | | | | |
| Change (kg) | −1.76 | 1.12 | 0.1255 | −2.23 | 1.12 | 0.0543 | 0.47 | 1.59 | 0.7695 |
| % Change | 0.02 | 0.01 | 0.217 | 0.00 | 0.01 | 0.9169 | 0.02 | 0.02 | 0.3473 |

Significance value (*$p < 0.05$; **$p < 0.01$). Data is expressed as mean ± SEM (standard error of the mean).
[1]Sum of all fat compartment masses.
[2]Sum of pelvic, visceral and thoracic fat masses.
[3]Sum of all integrated tissue masses. Between group difference = statistical significance between diets.

Table IX reports upon changes in body adipose tissue subcompartment surface area in overweight (n=20) men after six weeks.

TABLE IX

|  | Extra Virgin Olive oil | ±SEM | p value | Test Lipid | ±SEM | p value | Between group difference | ±SEM | p value |
|---|---|---|---|---|---|---|---|---|---|
| TAT[1] | | | | | | | | | |
| Change (cm$^2$) | −192.81 | 101.18 | 0.0658 | −232.45 | 101.18 | 0.0283* | 39.64 | 113.12 | 0.7299 |
| % Change | −2.698 | 1.6625 | 0.1148 | −4.2145 | 1.66 | 0.0165* | 1.52 | 1.80 | 0.4091 |
| SAT | | | | | | | | | |
| Change (cm$^2$) | −166.59 | 75.32 | 0.0343* | −206.59 | 75.32 | 0.0099** | 39.99 | 84.54 | 0.6416 |
| % Change | −3.3045 | 1.60 | 0.047* | −4.87 | 1.60 | 0.0046** | 1.57 | 1.82 | 0.3997 |
| AbAT[2] | | | | | | | | | |
| Change (cm$^2$) | −42.73 | 32.08 | 0.1927 | −9.15 | 32.08 | 0.7775 | −33.59 | 34.02 | 0.3359 |
| % Change | −4.63 | 3.58 | 0.2049 | −1.53 | 3.58 | 0.6711 | −3.09 | 4.49 | 0.4992 |
| IMAT | | | | | | | | | |
| Change (cm$^2$) | −9.53 | 15.17 | 0.5335 | −13.66 | 15.17 | 0.3736 | 4.13 | 21.40 | 0.8481 |
| % Change | −2.82 | 4.53 | 0.5386 | −3.84 | 4.54 | 0.4028 | 1.02 | 6.40 | 0.8738 |

Significance value (*$p < 0.05$; **$p < 0.01$). Data is expressed as mean ± SEM (standard error of the mean).
[1]Sum of all fat compartment areas.
[2]Sum of pelvic, visceral and thoracic fat areas. Between group difference = statistical significance between diets.

Energy Expenditure

The hourly average of fat oxidation in short-term feeding was higher with the test lipid than with the extra virgin olive oil at all time points except hour 6. There was a non-significantly higher fat oxidation during hour 1.5, 2.5, 3.5 and 4.5. The long-term feeding hourly average of fat oxidation continued to be higher with the test lipid, compared to extra virgin olive oil, but to a smaller extent than the short-term feeding. Fat oxidation was non-significantly greater during hours 1.5, 2.5, 3.5 and 4.5 in the long-term feeding. Total fat oxidation for the short-term test lipid measurement was non-significantly larger than short-term feeding extra virgin olive oil, while the data after long-term feeding for the extra virgin olive oil and the test lipid were similar. In addition, there was a statistically significant difference seen between the short-term feeding of the test lipid and long-term feeding of the test lipid, demonstrating a significant decrease in effect of the test lipid with time.

General Observations

Total cholesterol and LDL cholesterol levels were substantially reduced using the test lipid in accordance with the invention, statistically exceeding these cholesterol lowering effects of extra virgin olive oil, which is considered to be one of the "gold standard" oils for improving circulatory lipid patterns, although not a typical conventional fat in many geographic areas. The test lipids accomplished this significant reduction in total cholesterol and LDL cholesterol while experiencing only minimal reduction in HDL cholesterol levels. These data illustrate definite cardio-protective benefits of the test lipid by reducing the total cholesterol level by 17 percent and the LDL cholesterol level by 21 percent. This indicates a functional decrease in atherogenic risk. The data indicate that this is accompanied by a tendency to enhance the loss of total body mass and adipose mass through enhancement of energy expenditure.

It will be understood that the embodiments of the present invention which have been described are illustrative of some of the applications of the principles of the present invention. Numerous modifications may be made by those skilled in the art without departing from the true spirit and scope of the invention.

The invention claimed is:

1. A lipid composition, comprising an interesterified structured lipid component and a phytosterol ester component:
said structured lipid component is a reaction product of an interesterification reactant charge in the presence of an interesterification catalyst, said reactant charge having between about 15 and about 75 weight percent, based upon the total weight of the charge, of a medium chain triglyceride having one glycerol component with fatty acid moiety chains that are from C6 to C12 in length, reacted with between about 15 and about 85 weight percent, based upon the total weight of the charge, of a long chain domestic oil having another glycerol component with fatty acid moiety chains of at least C16 in length, said structured lipid component being an interesterified randomization product wherein fatty acid moiety chains from said one glycerol component are exchanged with fatty acid moiety chains from said other glycerol component, resulting in triglycerol structures which have interexchanged fatty acid moiety chains that vary randomly from glycerol structure to glycerol structure; and said interesterified structured lipid component comprises at least about 80 weight percent of the lipid composition, and said phytosterol ester component comprises between about 4 and about 20 weight percent of the lipid composition, both based on the total weight of the lipid composition.

2. The composition of claim 1, when ingested by a hypercholesterolemic individual at a level of at least about 0.4 grams of the composition per kilogram of body weight of the individual for at least about six weeks, reduces the LDL cholesterol level of said individual by at least about 8 percent.

3. The composition in accordance with claim 2, wherein said composition reduces the total cholesterol level of said individual by at least about 10 percent.

4. The composition in accordance with claim 2, wherein said composition does not significantly reduce the HDL cholesterol level of said individual.

5. The composition in accordance with claim 2, wherein said composition reduces adipose mass of said individual.

6. The composition in accordance with claim 1, wherein said structured lipid component comprises at least about 88 weight percent of the composition, and said phytosterol ester component comprises up to about 12 weight percent of the composition, both based upon the total weight of the composition.

7. The composition in accordance with claim 1, wherein said structured lipid component comprises at least about 90 weight percent of the composition, and said phytosterol ester comprises up to about 10 weight percent of the composition, both based upon the total weight of the composition.

8. The composition in accordance with claim 1, wherein said structured lipid component comprises at least about 92 weight percent of the composition and said phytosterol ester comprises up to about 8 weight percent of the composition, both based upon the total weight of the composition.

9. The composition in accordance with claim 1, wherein said medium chain triglyceride amount is between about 30 and about 60 weight percent of the interesterification charge, and the amount of the domestic oil is between about 40 and about 70 weight percent of the charge.

10. The composition in accordance with claim 1, wherein said medium chain triglyceride amount is between about 35 and about 55 weight percent of the interesterification charge, and the amount of the domestic oil is between about 45 and about 65 weight percent of the charge.

11. The composition in accordance with claim 1, wherein said structured lipid component has a Brookfield viscosity of between about 20 and about 52 centipoise, measured at 20° C. with a No. 4 spindle at 50 rpm on a Brookfield Viscometer.

12. The composition in accordance with claim 1, wherein said structured lipid component has a smoke point of at least about 195° C. (at least about 383° F.)

13. The composition in accordance with claim 1, wherein said structured lipid component has a smoke point of at least about 205° C. (at least about 400° F.)

14. The composition in accordance with claim 1, wherein said phytosterol ester component has no greater than about 20% by weight, based upon the total weight of the phytosterol ester component, of a phytostanol.

15. The composition in accordance with claim 2, wherein said composition is administered to the individual at a level of between about 0.4 grams and about 2 grams of said composition per kilogram of body weight per day for at least about 6 weeks.

16. The composition in accordance with claim 1, wherein said lipid composition is a clear liquid and remains a clear liquid for at least about six months of storage at about 21° C.

17. The composition in accordance with claim 1, wherein said lipid composition has sensory attributes which are not significantly different from, or are significantly superior to, corresponding sensory properties of canola oil and/or of olive oil when used in food and when evaluated by a trained sensory panel.

18. The composition in accordance with claim 1, wherein said medium chain triglyceride is selected from the group consisting of caprylic triglyceride, capric triglyceride, and combinations thereof, wherein said domestic oil is selected from the group consisting of soybean oil, corn oil, cottonseed oil, canola oil, olive oil, peanut oil, safflower oil, sunflower oil, oil from grain plants, and combinations thereof.

19. A method for using the lipid composition of claim 1, comprising administering the lipid composition to an individual in order to promote the health and nutrition of said individual, including decreasing the atherogenic risk to the individual by reducing adipose mass of said individual.

20. The method in accordance with claim 19, wherein said individual is hypercholesterolemic and said administering at a level of at least about 0.4 grams of the composition per kilogram of body weight of the individual for at least about six weeks reduces the LDL cholesterol of said individual by at least about 10 percent.

21. The method in accordance with claim 19, wherein said individual is hypercholesteroliemic and said administering at a level of at least about 0.4 grams of the composition per kilogram of body weight of the individual for at least about six weeks reduces the total cholesterol of said individual by at least about 8 percent.

22. The method in accordance with claim 19, wherein said administering at a level of at least about 0.4 grams of the composition per kilogram of body weight of the individual for at least about six weeks does not significantly reduce the HDL cholesterol level of said individual.

23. The method in accordance with claim 19, wherein said administering is at a level of at least about 0.4 grams of said lipid composition per kilogram of body weight of said individual.

24. The method in accordance with claim 19, wherein said administering is at a level of between about 0.4 and about 2 grams of said lipid composition per kilogram of body weight of said individual.

25. The method in accordance with claim 19, wherein said administering is at a level of between about 0.6 and about 1 gram of said lipid composition per kilogram of body weight of said individual.

26. The composition of claim 1, when ingested by a hypercholesterolemic individual at a level of at least about 0.4 grams of the composition per kilogram of body weight of the individual for at least about six weeks, reduces the LDL cholesterol level of said individual by at least about 15 percent.

27. The composition in accordance with claim 2, wherein said lipid composition reduces the total cholesterol level of said individual by at least about 12 percent.

28. The composition in accordance with claim 3, wherein said lipid composition does not significantly reduce the HDL cholesterol level of said individual.

29. The composition in accordance with claim 3, wherein said lipid composition reduces adipose mass of said individual.

30. The composition in accordance with claim 4, wherein said lipid composition reduces adipose mass of said individual.

31. The composition in accordance with claim 2, wherein said structured lipid component comprises at least about 90 weight percent of the composition, and said phytosterol ester comprises up to about 10 weight percent of the composition, both based upon the total weight of the composition.

32. The composition in accordance with claim 2, wherein said structured lipid component has a Brookfield viscosity of between about 20 and about 52 centipoise, measured at 20° C. with a No. 4 spindle at 50 rpm on a Brookfield Viscometer.

33. The composition in accordance with claim 2, wherein said structured lipid component has a smoke point of at least about 195° C. (at least about 383° F.)

34. A method for making a lipid composition for reducing atherogenic risk in individuals, comprising:
   providing a medium chain triglyceride having one glycerol component with fatty acid moiety chains that have carbon chain lengths of between C6 and C12;
   providing domestic oil having another glycerol component with fatty acid moiety chains that have carbon chain lengths of between C16 and C22;
   introducing a reactant charge to a reaction location, the reactant charge including between about 15 and about 85 weight percent of the medium chain triglyceride and between about 15 and about 85 weight percent of said domestic oil, based upon the total weight of the reactant charge;
   interesterifying said reactant charge in the presence of an interesterification catalyst into an interesterified structured lipid randomization product wherein fatty acid moiety chains from said one glycerol component are exchanged with fatty acid moiety chains from said another gylcerol component, resulting in triglycerol structures which have interexchanged fatty acid moiety chains that vary randomly from glycerol structure to glycerol structure; and
   combining said interesterified structured lipid component with a phytosterol ester component to provide a lipid composition, said combining being such that said the lipid composition contains at least about 80 weight percent of the structured lipid component and up to about 20 weight percent of the phytosterol ester component, based on the total weight of the lipid composition.

35. The method in accordance with claim 34, wherein said lipid composition has a Brookfield viscosity of between about 20 and about 52 centipoise, measured at 20° with a No. 4 spindle at 50 rpm on a Brookfield Viscometer.

36. The method in accordance with claim 34, wherein said lipid composition has a smoke point of at least about 195° C. (at least about 383° F.)

37. The composition in accordance with claim 2, wherein said lipid composition has sensory attributes which are not significantly different from, or are significantly superior to, corresponding sensory properties of canola oil and/or of olive oil when used in food and when evaluated by a trained sensory panel.

38. The method in accordance with claim 35, wherein said lipid composition has a smoke point of at least about 195° C. (at least about 383° F.)

* * * * *